US011426262B2

(12) United States Patent
Simmonds et al.

(10) Patent No.: US 11,426,262 B2
(45) Date of Patent: Aug. 30, 2022

(54) DIGITAL DESIGN AND MANUFACTURING PROCESS FOR DENTURE ABUTMENT LUTING BAR

(71) Applicant: EVOLLUTION IP HOLDINGS, INC., Birmingham, AL (US)

(72) Inventors: Boris A. Simmonds, Vestavia, AL (US); John J. Bellanca, Birmingham, AL (US)

(73) Assignee: EVOLLUTION IP HOLDINGS, INC., Birmingham, AL (US)

( * ) Notice: Subject to any disclaimer, the term of this patent is extended or adjusted under 35 U.S.C. 154(b) by 856 days.

(21) Appl. No.: 15/921,510

(22) Filed: Mar. 14, 2018

(65) Prior Publication Data

US 2018/0263737 A1  Sep. 20, 2018

Related U.S. Application Data

(60) Provisional application No. 62/472,073, filed on Mar. 16, 2017.

(51) Int. Cl.
*A61C 8/00* (2006.01)
*A61C 9/00* (2006.01)
(Continued)

(52) U.S. Cl.
CPC ............ *A61C 8/0095* (2013.01); *A61C 8/005* (2013.01); *A61C 8/0048* (2013.01);
(Continued)

(58) Field of Classification Search
CPC ..... A61C 8/0095; A61C 8/0048; A61C 8/005; A61C 9/0053; A61C 13/0004;
(Continued)

(56) References Cited

U.S. PATENT DOCUMENTS 5,219,286 A * 6/1993 Hader ............... A61C 8/0048
433/172
5,234,339 A   8/1993 Grigereit
(Continued)

OTHER PUBLICATIONS

"The Cal-Technique"; Attachments International, Inc. Newsletter; vol. 19; Summer 1998; 4 pgs.

*Primary Examiner* — Heidi M Eide
*Assistant Examiner* — Drew S Folgmann
(74) *Attorney, Agent, or Firm* — Gardner Groff & Greenwald, PC

(57) ABSTRACT

Taking an intraoral scan of a patient's mouth with existing implants, creating a digital model of the patient's mouth, digitally designing a denture bar based on the digital mouth model, fabricating a physical bar based on the digital bar model, delivering the physical bar into the patient's mouth, capturing records of the patient's mouth and installed physical bar, producing a physical denture and joining it to the physical bar, and delivering the physical denture and bar into the patient's mouth, all in no more than three dental office visits. The step of digitally designing a denture bar typically includes selecting a cement gap for the abutments based on errors in the digital mouth model resulting from the intraoral scan, as well as designing lateral cement ports into the
(Continued)

digital bar model. And the step of fabricating a physical bar typically includes using additive manufacturing such as 3D printing.

11 Claims, 20 Drawing Sheets

(51) Int. Cl.
*G16H 50/50* (2018.01)
*A61C 13/34* (2006.01)
*A61C 13/00* (2006.01)
*G16H 10/60* (2018.01)
*G16H 40/63* (2018.01)

(52) U.S. Cl.
CPC ........ *A61C 9/0053* (2013.01); *A61C 13/0004* (2013.01); *A61C 13/0019* (2013.01); *A61C 13/34* (2013.01); *G16H 10/60* (2018.01); *G16H 40/63* (2018.01); *G16H 50/50* (2018.01)

(58) Field of Classification Search
CPC .... A61C 13/0019; A61C 13/34; G16H 50/50; G16H 10/60; G16H 40/63
See application file for complete search history.

(56) References Cited

U.S. PATENT DOCUMENTS

| | | | |
|---|---|---|---|
| 5,419,700 A | 5/1995 | Sillard | |
| 5,630,717 A | 5/1997 | Zuest et al. | |
| 6,319,000 B1 * | 11/2001 | Br.ang.nemark | A61C 1/084 |
| | | | 433/75 |
| 6,672,870 B2 | 1/2004 | Knapp | |
| 6,902,401 B2 | 6/2005 | Jorneus et al. | |
| 7,214,061 B2 | 5/2007 | Fortin | |
| 8,529,255 B2 | 9/2013 | Poirier et al. | |
| 2012/0058449 A1 | 3/2012 | Sklarski et al. | |
| 2012/0179281 A1 * | 7/2012 | Steingart | A61C 13/0004 |
| | | | 700/97 |
| 2014/0106303 A1 | 4/2014 | Giasson et al. | |
| 2014/0178839 A1 | 6/2014 | Berger | |
| 2015/0044636 A1 | 2/2015 | Castelnuovo | |
| 2015/0147723 A1 | 5/2015 | Berger | |
| 2016/0135931 A1 * | 5/2016 | Morales | A61C 8/0089 |
| | | | 433/213 |
| 2016/0250002 A1 | 9/2016 | Cota | |
| 2016/0270886 A1 * | 9/2016 | Schulter | A61C 13/34 |
| 2018/0042707 A1 | 2/2018 | Schnitzspan | |
| 2018/0049849 A1 | 2/2018 | Lamar et al. | |

* cited by examiner

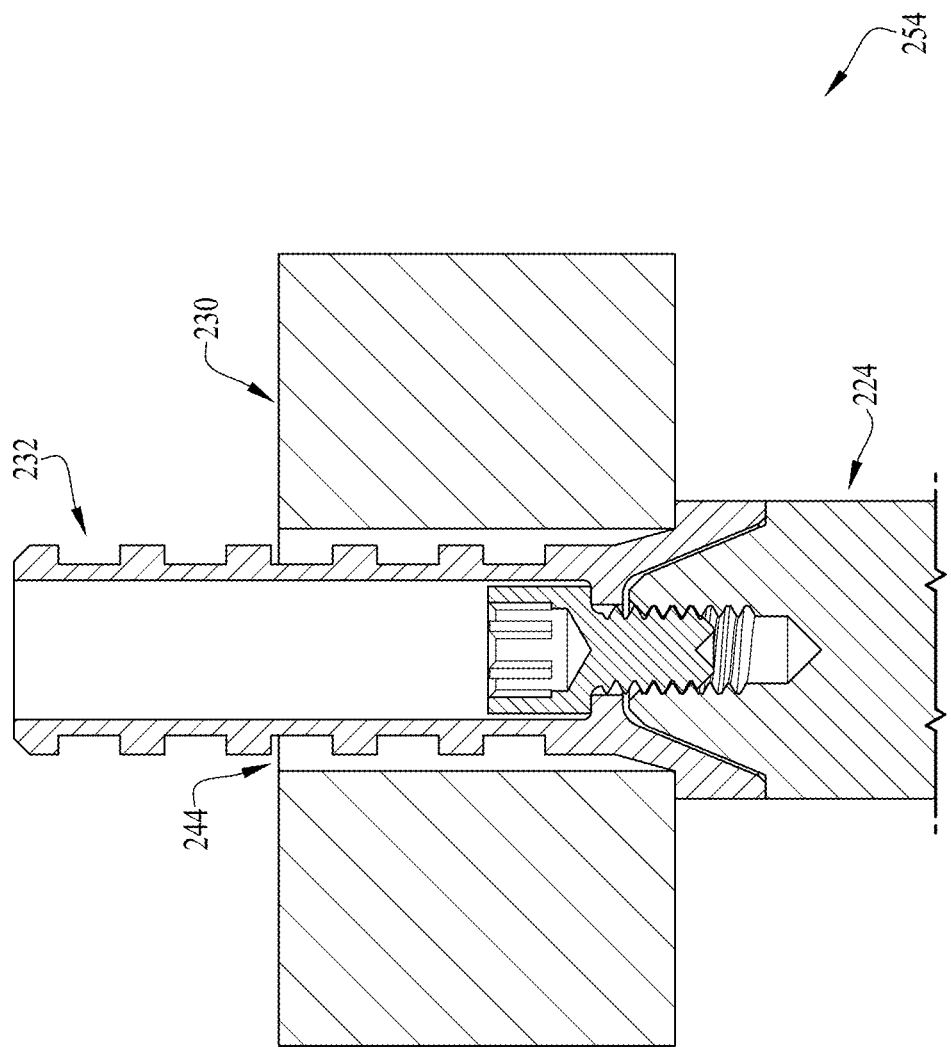

ial Patent Application Ser. No. 62/472,073 filed Mar. 16, 2017, the entirety of which is hereby incorporated herein by reference for all purposes.

DIGITAL DESIGN AND MANUFACTURING PROCESS FOR DENTURE ABUTMENT LUTING BAR

CROSS-REFERENCE TO RELATED APPLICATION

This application claims the priority benefit of U.S. Provisional Patent Application Ser. No. 62/472,073 filed Mar. 16, 2017, the entirety of which is hereby incorporated herein by reference for all purposes.

TECHNICAL FIELD

The present invention relates generally to the field of implant dentistry, and more particularly to designing, manufacturing, and installing denture bars for overdenture dental implants.

BACKGROUND

Modern prosthetic dentures can be permanently mounted in a patient's mouth via a customized denture bar that mounts to dental abutments that in turn mount to dental implants that are placed in the patient's jawbone. Traditionally, this involved making an impression mold of the patient's mouth, creating a model of the patient's mouth from the mouth mold, and designing and casting a bar based on the mouth model. But this process introduces inaccuracies, so the customized bar had to be sectioned and soldered back together to get a precise fit.

In an effort to improve on this, the KAL/CAL (Kulzer Abutment Luting/California Abutment Luting) technique was introduced. This involves positioning shim spacers on the abutments before making a wax-up of the bar, which when removed leave gaps in the model bar. Basically, this involves oversizing the abutment holes in the bars to account for imprecision in the process, to thereby provide a bar with a "passive" fit on the abutments, with the oversized gap then filled with cement in the luting process to provide a resulting precise fit.

More recent developments have involved creating a digital model of the physical model of the patient's mouth using a highly accurate desktop/laboratory scanning system, digitally designing the bar based on the digital model, and milling the bar from one piece of material. This is disclosed for example in U.S. Pat. No. 6,902,401, which is hereby incorporated herein by reference. This results in a custom bar that precisely fits the abutments, and so the cement gaps are not needed or included in the bar design. However, this process (leading up to the ability to generate a custom bar, regardless if a cast or CAD/CAM bar) still has its drawbacks. For example, it requires numerous office visits to complete, and the laboratory model used to generate the custom bar must still be verified by a verification jig.

Accordingly, it can be seen that needs exist for improvements in the designing, manufacturing, and installing of custom denture bars. It is to the provision of solutions meeting these and other needs that the present invention is primarily directed.

SUMMARY

Generally described, the invention relates to a digital design and manufacturing process for denture abutment luting bars, and such denture bars designed and manufactured by the process. In exampled embodiments, the process includes taking an intraoral scan of a patient's mouth with existing implants, creating a digital model of the patient's mouth based on the intraoral scan, digitally designing a denture bar based on the digital mouth model, fabricating a physical bar based on the digital bar model, delivering the physical bar into the patient's mouth, capturing records of the patient's mouth and installed physical bar, producing a physical denture and joining it to the physical bar, and delivering the physical denture and bar into the patient's mouth, all in no more than three dental office visits. The step of digitally designing a denture bar typically includes selecting a cement gap for the abutments based on errors in the digital mouth model resulting from the intraoral scan, as well as designing lateral cement ports into the digital bar model for use in the luting process. And the step of fabricating a physical bar typically includes using additive manufacturing such as 3D printing.

These and other aspects, features, and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of example embodiments are explanatory of example embodiments of the invention, and are not restrictive of the invention, as claimed.

BRIEF DESCRIPTION OF THE DRAWINGS

FIG. 11 is a screen display showing in cross-section the digital bar model segment and abutment of FIG. 10A with a tight spacing selected for the cement gap.

DETAILED DESCRIPTION OF EXAMPLE EMBODIMENTS

The present invention may be understood more readily by reference to the following detailed description of example embodiments taken in connection with the accompanying drawing figures, which form a part of this disclosure. It is to be understood that this invention is not limited to the specific devices, methods, conditions, and/or parameters described and/or shown herein. Any and all patents and other publications identified in this specification are incorporated by reference as though fully set forth herein.

The terminology used herein is for purposes of describing particular embodiments only, and is not intended to be limiting. The defined terms are in addition to the technical, scientific, or ordinary meanings of the defined terms as commonly understood and accepted in the relevant context.

The words "example" and "exemplary," as used herein, are intended to be non-exclusionary and non-limiting in nature. More particularly, these words indicate one among several examples, with no undue emphasis or preference being directed to the particular example being described.

The singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

"Denture" means a prosthetic restorative oral appliance of artificial teeth, typically a base supporting a complete arch of teeth (a full denture), also including a base with only a portion of a full arch of teeth (i.e., at least two teeth) with the base spanning at least two implants (a partial denture), and can also be referred to as an overdenture.

"Abutment" means a post component onto which a denture bar mounts, and is used generally to include base abutments that mount onto implants, extension abutments that mount onto base abutments, and copings that mount onto abutments or implants.

"Physical" means an actual structure existing in the real world.

"Digital" means existing only in electronic form as a virtual model or representation of a real physical structure.

"Bar" means a platform that is integrate into a denture for mounting the denture to dental implants via dental abutments.

Figure 1:
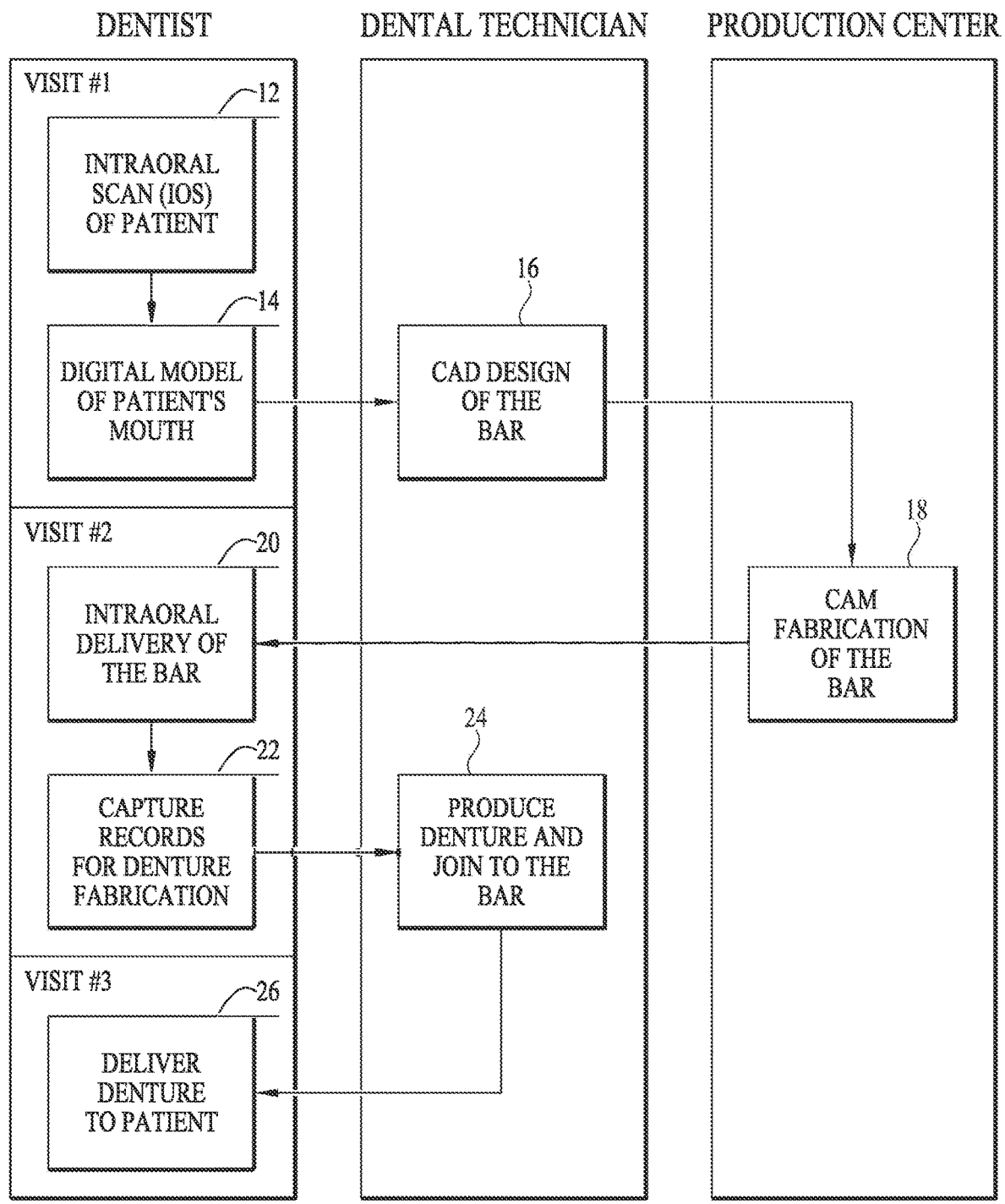
FIG. 1 is a process flow diagram of a denture bar design and manufacture method according to an example embodiment of the present invention.

With reference now to the drawing figures, wherein like reference numbers represent corresponding parts throughout the several views, FIG. 1 shows a method 10 of designing, manufacturing, and installing a denture for a denture according to an example embodiment of the invention, and FIGS. 2-25 show examples of the steps of the method 10 being performed. For ease of reference, physical elements are identified by reference characters in the 100s and digital elements are identified by the corresponding reference character in the 200s.

The method 10 begins at step 12 with a patient who presents with a gum-ridge with existing dental implants. In typical cases, the patient has worn an unsecured denture that is being replaced by a more permanent implant-secured denture, and the dental implants were placed as a preliminary step. In cases where the patient received the implants by means of a dental surgical guide, the method 10 can begin at step 14, with the digital model of the patient's mouth is provided through use of a commercially available guided surgical software such as 3Shape Implant Studio (3Shape A/S; Copenhagen, Denmark).

Figure 2:
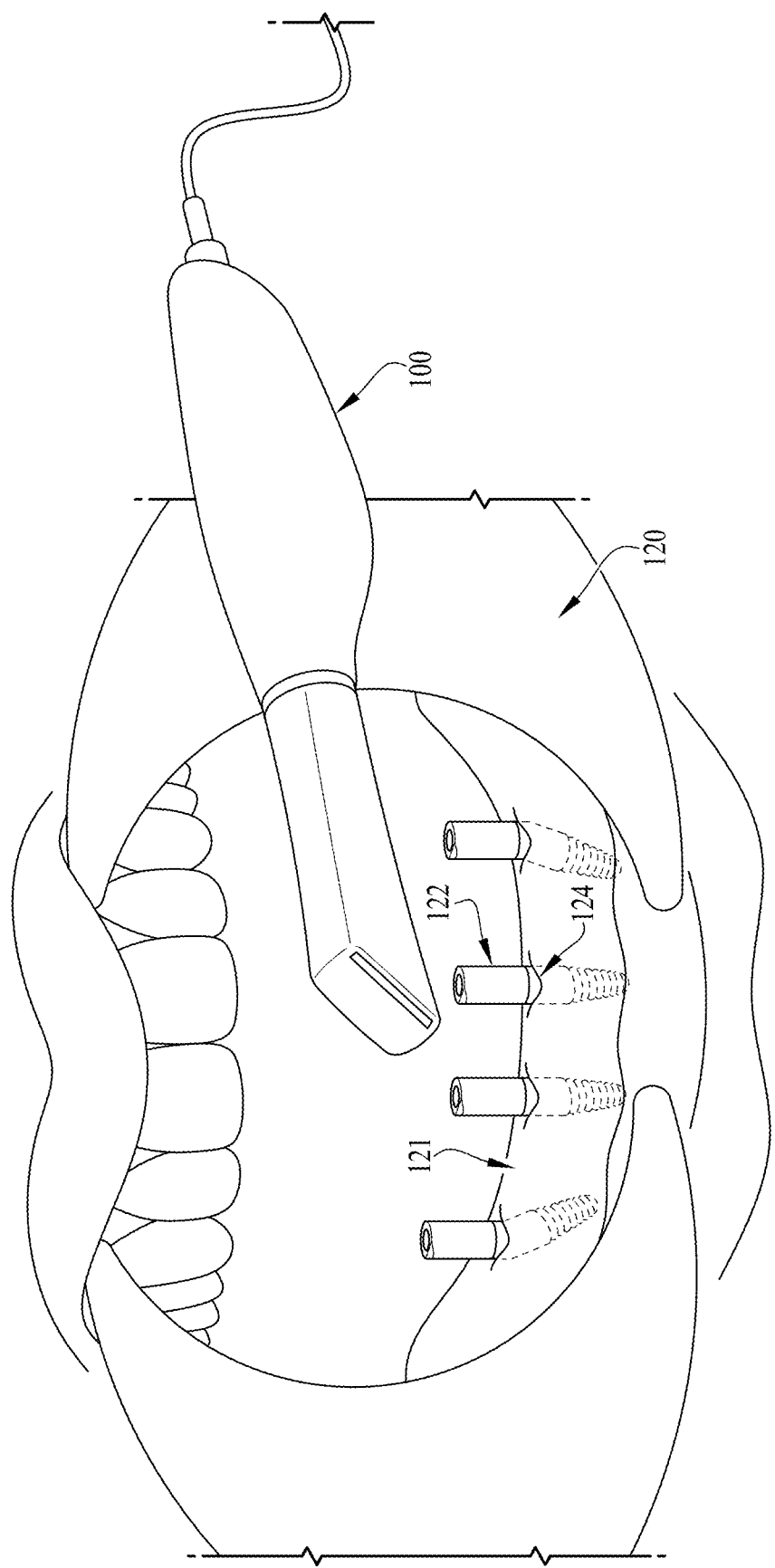
FIG. 2 is a perspective view of a patient's mouth being directly scanned by an intraoral scanner in a first office visit, with the mouth including scan bodies installed on abutments, in accordance with a step of the method of FIG. 1.

At step 12, the method 10 includes using an intraoral scanner 100, inserted into the patient's mouth 120, to capture electronic 3D image data directly from the patient's mouth 120, for example as shown in FIG. 2. This step is typically done in the dentist's office during a first office visit for performing the method 10 (preliminary consultations not considered part of the procedure). Physical scan bodies 122 are first installed (e.g., screw-mounted) onto physical abutments 124, which in turn were first installed (e.g., screw-mounted) onto the physical implants (not shown) in the jawbone along the gum-ridge 121 of the mouth 120. In this way, the electronic 3D image data captured by the intraoral scanner 100 includes data representing the physical position and orientation of the scan bodies 122, and thus of the implants the scan bodies are attached to. The scan bodies 122 can be of a conventional type for example ELOS Accurate Position Locators commercially available from Nobel Biocare Service AG. And the intraoral scanner 100 can be of a conventional type for example a TRIOS scanner commercially available from 3Shape A/S (Copenhagen, Denmark).

In other embodiments, scan bodies are not used and instead the exposed top portions of the abutments 124, cover caps, healing caps, or the like are directly scanned by the intraoral scanner 100. In still other embodiments, the intraoral scanner 100 (or a desktop scanner) is used to capture electronic 3D image data indirectly, for example from a stone or other physical model of the patient's mouth 120 made from a polyvinyl or other physical impression, with the impression made during the office visit and the model and scan made in a remote lab. And in still other embodiments, a digital model of the patient's mouth is obtained through use of a commercially available guided surgical software, such as 3Shape Implant Studio (3Shape A/S; Copenhagen, Denmark), when the patient receives the implants, and as such the method 10 begins at step 14.

Figure 3:
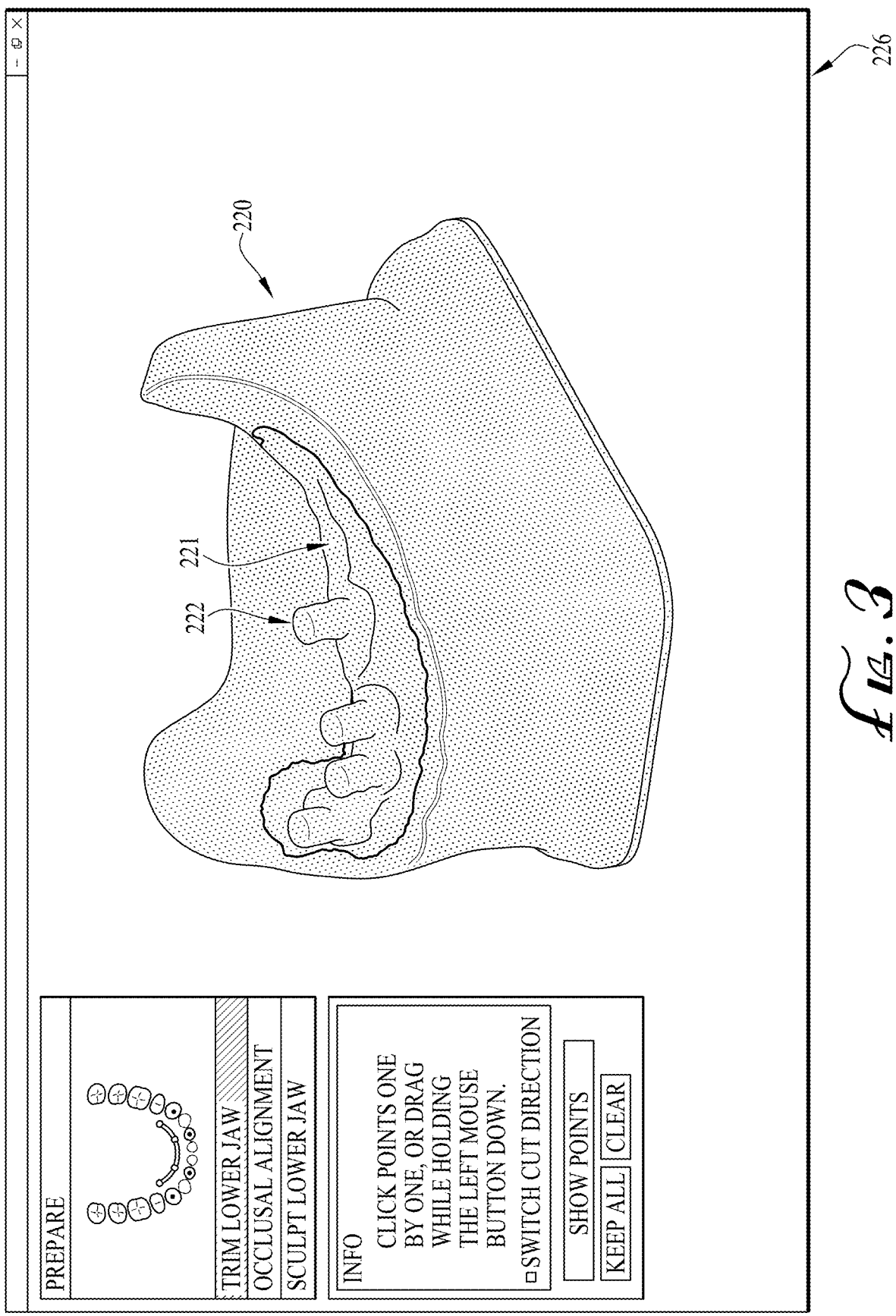
FIG. 3 is a screen display of a raw digital model of the patient's mouth created based on the direct intraoral scan of FIG. 2, in accordance with a next step of the method.
Figure 4:
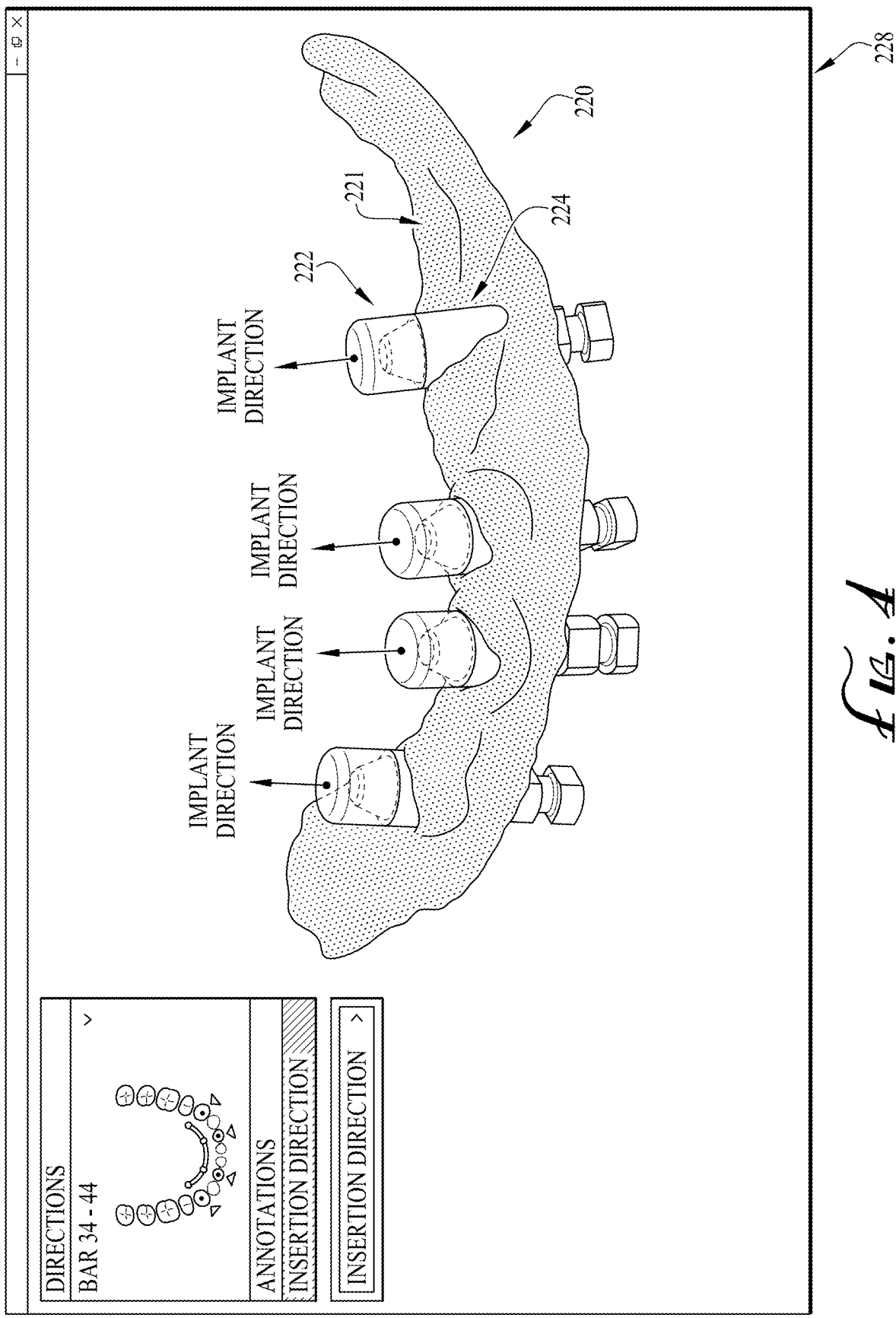
FIG. 4 is a screen display of a finished digital model of the patient's mouth based on the raw digital model of FIG. 3, with digital scan bodies shown identifying the orientation of digital abutments.

Next at step 14 a digital 3D model 220 of the patient's mouth 120 is rendered from the captured electronic 3D image data, for example as shown in the computer screen displays 226 and 228 of FIGS. 3-4. This is done using dental CAD software on a conventional computer workstation desk. The electronic 3D image data captured by the intraoral scanner 100 can be transmitted to the workstation and imported into the CAD software in any conventional well-known manner. This step 14 can be done during the first patient visit at the dentist's office (as depicted in FIG. 1), or this can be done later and/or remotely, whether by the dentist or by a dental technician.

An example of the dental CAD software that can be used in the method 10 is 3SHAPE dental system software commercially available from 3Shape A/S (Copenhagen, Denmark). This CAD software can be customized with libraries of user-defined components such as digital models of the physical scan bodies 122, abutments 124, cover caps, healing caps, implants, etc. As an illustrative example of this step 14 implemented using this CAD software, the screen 226 of FIG. 3 is displaying a raw digital model 220 of the patient's mouth 120 that has been rendered based on the raw electronic 3D image data, with rough depictions of the digital gum-ridge 221 and the digital scan bodies 122 based on the raw scan data. And the screen 228 of FIG. 4 is displaying the finished digital model 220 (actually, a demarcated portion of it) of the patient's mouth 120 after the raw digital model has been processed for example cleaned up using a smoothening function of the software. Thus, the finished digital model 220 of the patient's mouth 120 shows the position and orientation of the digital scan bodies 222 and the aligned digital abutments 224. It should be noted that the digital abutments 224 depicted are abutment "replicas" for use in diagnostic models, with an upper portion that simulates the physical abutment 124 that is connected to the implant, and with a lower portion that does not.

Next at step 16 a digital 3D denture bar 230 is designed for the digital mouth model 220, with its digital abutments 224 along its digital gum-ridge 221, using dental CAD software. This step 16 is typically done after the first patient visit, by a dental technician at a remote lab, though it can be done at the local dentist's office.

For example, the dental CAD software can be the 3SHAPE dental system software used in the previous step 14. FIGS. 5-15 provide illustrative examples of this step 16 implemented using this CAD software. This CAD software can be customized with libraries of user-defined model components such as digital denture bars 230, digital abutments 232, digital vertical through-holes 242 (e.g., one for each of the abutments), etc. It should be noted that the depicted copings or abutments 232 attach (e.g., screw-mount) to the depicted abutments 224, and for clarity herein these components will be referred to as the base abutments 224 and the extension abutments 232, respectively. In the example embodiment, the digital bar 230 mounts to the extension abutments 232, though in other example embodiments it can mount to base abutments or other types of extension abutments (e.g., copings).

Figure 5:
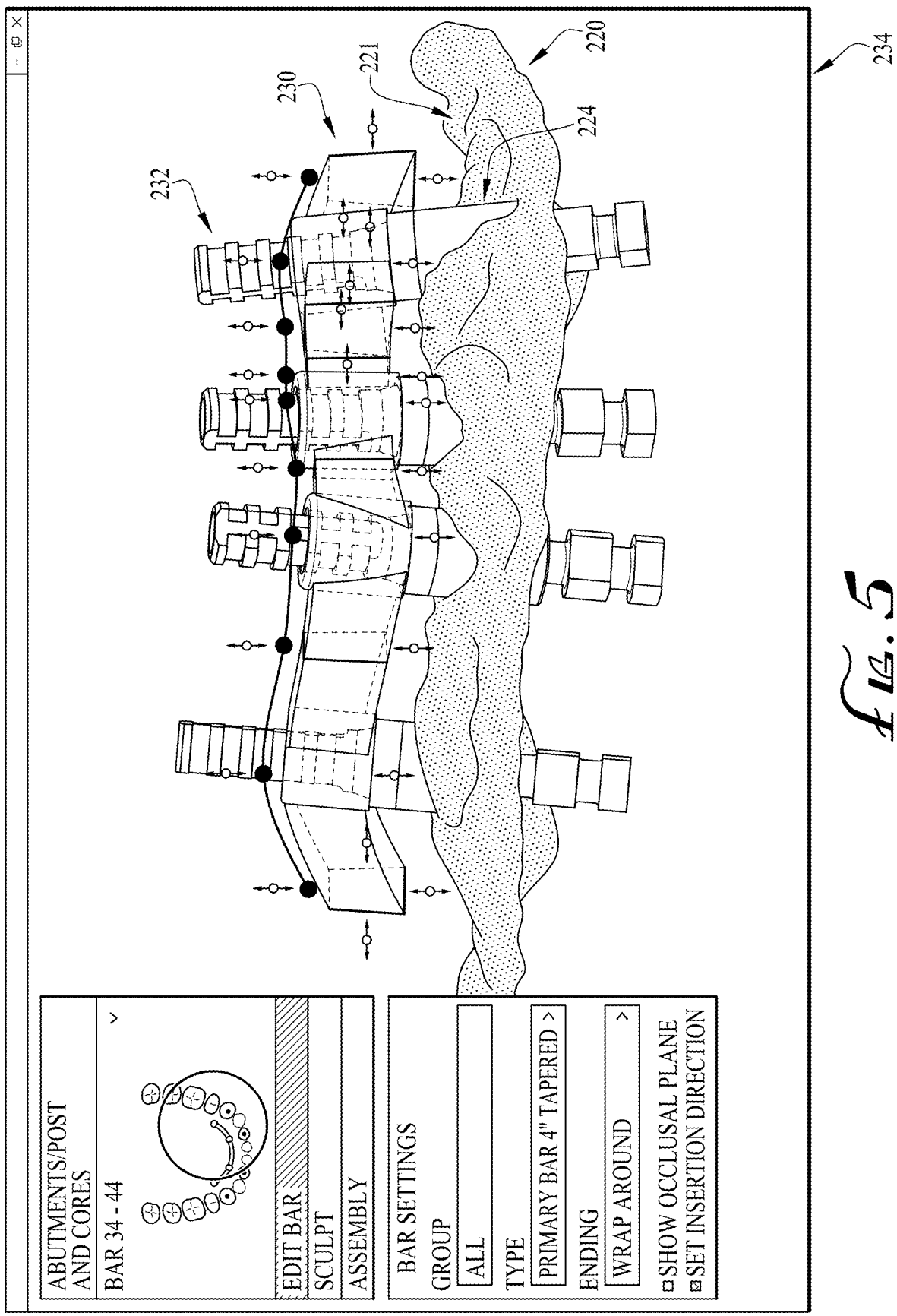
FIG. 5 is a screen display of a digital model of a custom denture bar being digitally designed based on the digital mouth model of FIG. 4, with digital extension abutments shown positioned based on the orientation of the underlying base digital abutments, in accordance with a next step of the method.
Figure 6:
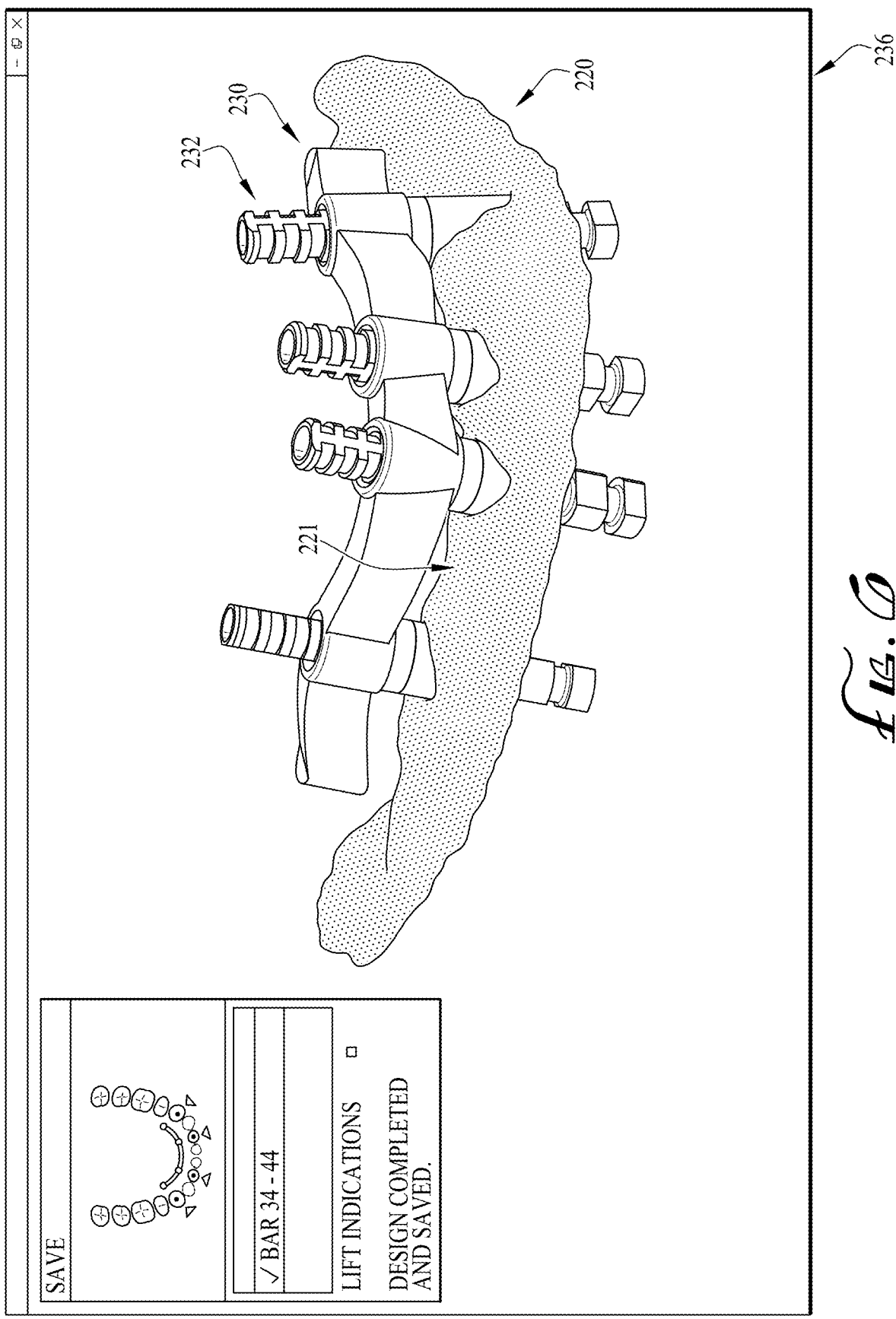
FIG. 6 is a screen display of a finished digital model of the denture bar and the basis digital mouth model of FIG. 5.
Figure 7:
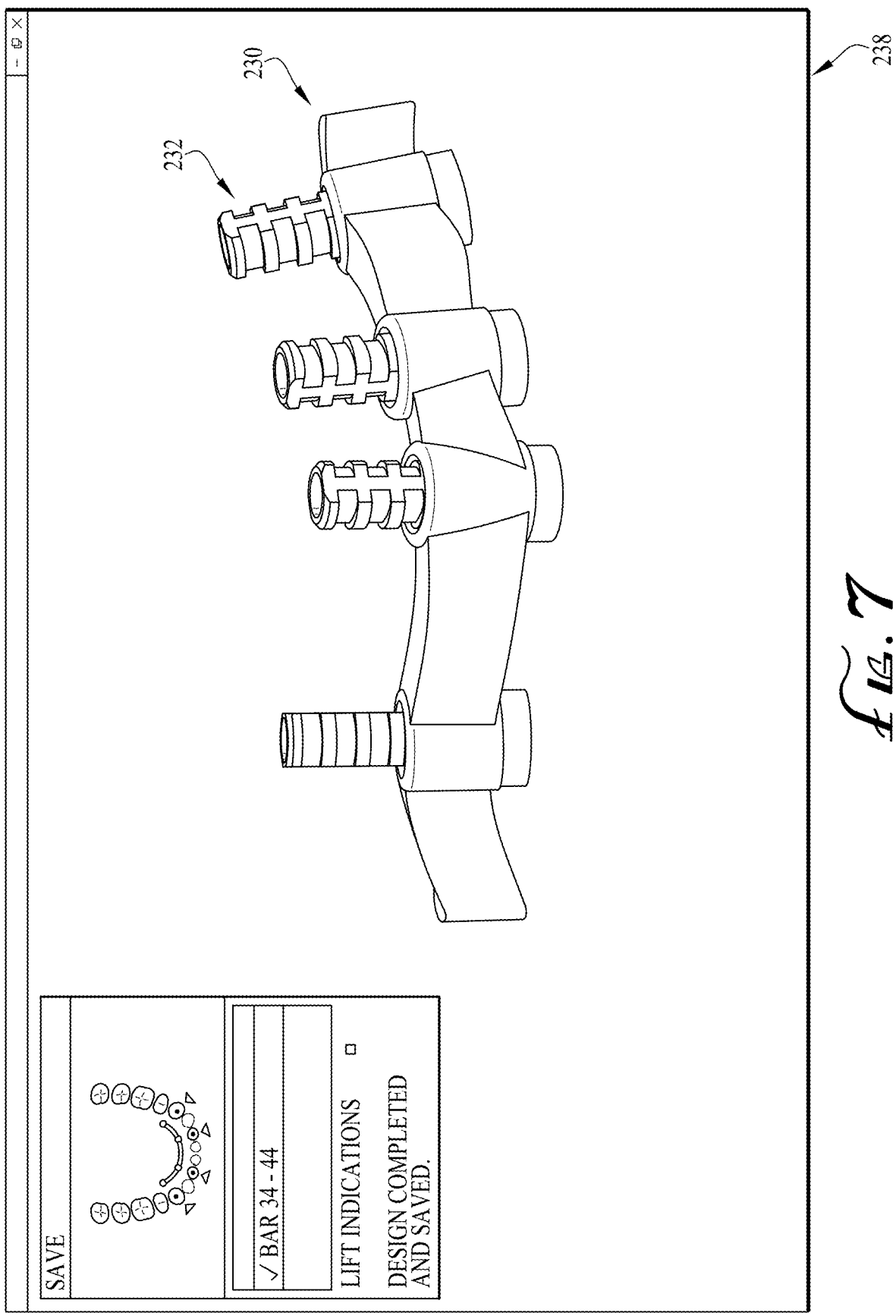
FIG. 7 is a screen display of the digital bar model of FIG. 6.
Figure 8:
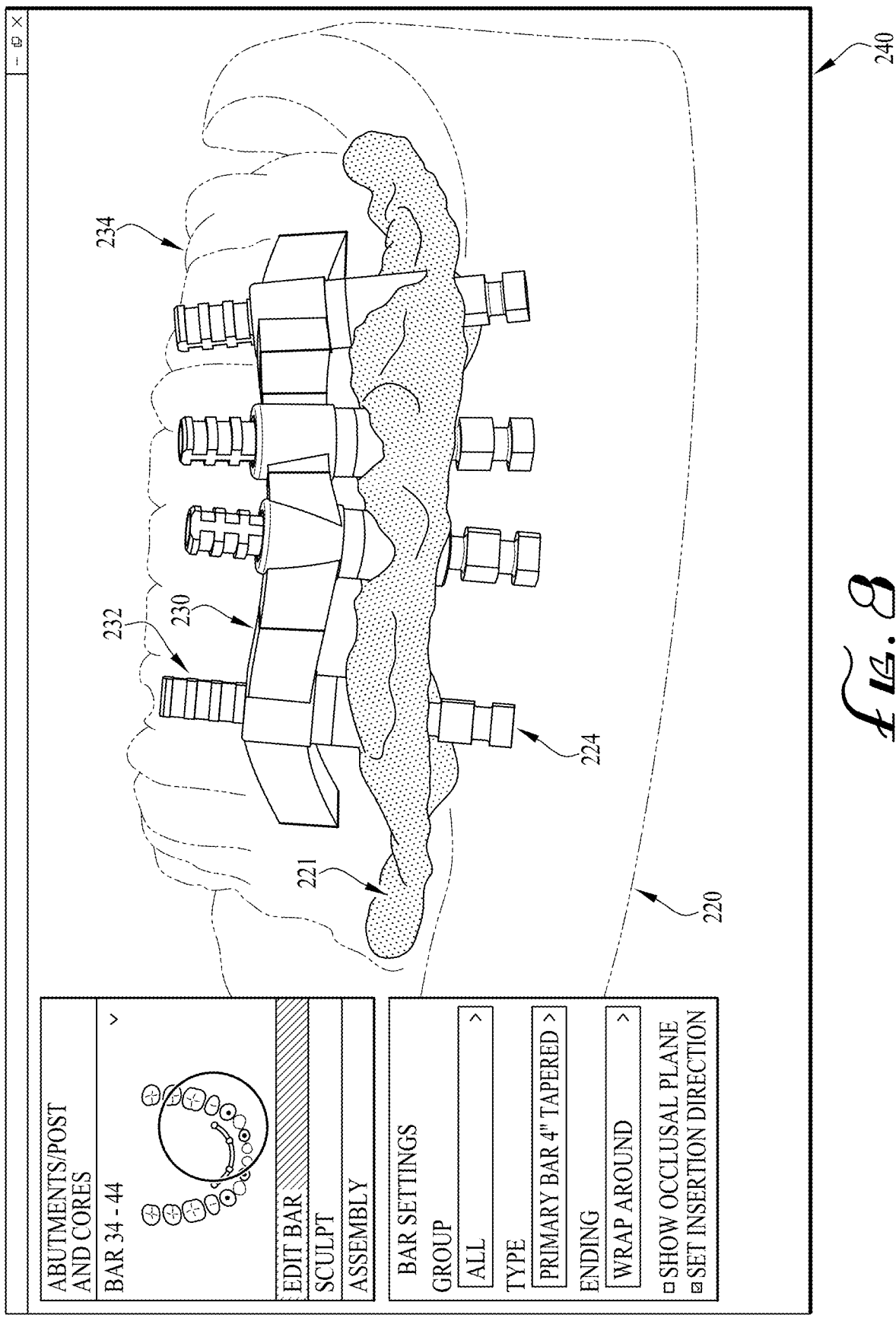
FIG. 8 is a screen display of the digital bar model and the digital mouth model of FIG. 6, with a virtual model of a denture shown covering the digital bar model.
Figure 9:
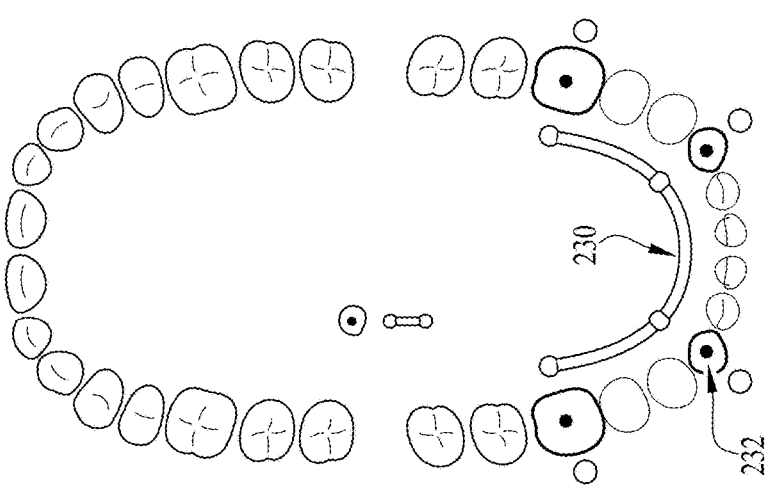
FIG. 9 is a screen display showing details of the design process of the digital bar model of FIG. 5, showing a selection process of one of multiple cement gap sizes.

The screen display 234 of FIG. 5 shows digital extension abutments 232 having been selected from the component library then aligned with and positioned on the digital base abutments 224, with the digital bar 230 now in the process of being digitally designed to fit the digital extension abutments 232 (without interference from the digital gum-line 221) of the digital mouth 220. The design of the digital bar 232 can be performed for example using toggles such as those depicted, with the CAD software used to customize the selected stock bar for the geometry of the digital mouth model 220 at hand. The screen display 236 of FIG. 6 shows the finished digital bar design/model 230 and the digital extension abutments 232 of the digital mouth 220. The screen display 238 of FIG. 7 shows in more detail the designed digital bar 230. And the screen display 240 of FIG. 8 shows a complete final digital assembly including the denture model 234 covering the digital bar 230 mounted to the digital extension abutments 232, which are mounted to the digital base abutments 224 that are mounted to the implants (not shown).

An additional innovative feature of the digital bar design step 16 is detailed in FIGS. 9-14. As shown, the digital bar 230 is designed with vertical through-holes 242 that receive the abutments 232. Because current technology and practice provide for precision imaging and design, conventional digital bars and implant connections are milled from one-piece titanium with a very close and snug fit (i.e., about 5 microns or less) that leaves no room for any discernable movement of the resulting physical bar relative to the implants. But the intraoral scanning step 12 provides less imaging accuracy than conventional desktop scanning equipment, so that precision advantage is lessened, and as such milling from one piece of metal is not possible. But the inaccuracy thus introduced is overcome by digitally designing cement gaps 244 in the digital bar 230, in a unique implementation, to result in a physical bar with cements gaps sized to provide a passive fit of the bar relative to the abutments 232, for example with the cement gaps selectively chosen for minimum workable size for the given application (i.e., with customized and minimalized oversizing of the vertical through-holes).

Figure 10B:
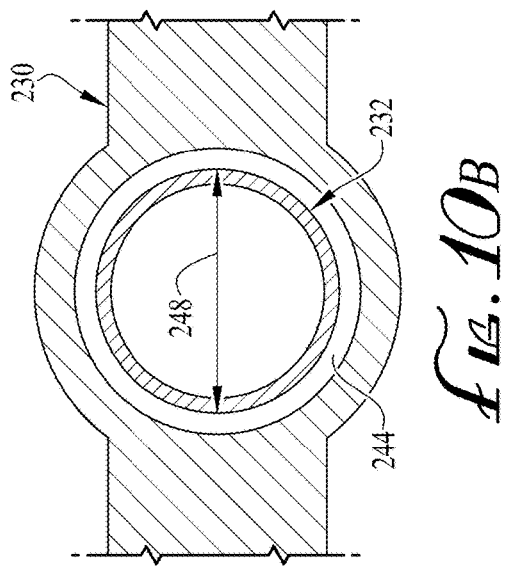
FIG. 10B is a schematic detail showing a cross-section of the digital bar model segment and the digital abutment model of FIG. 10A.
Figure 10C:
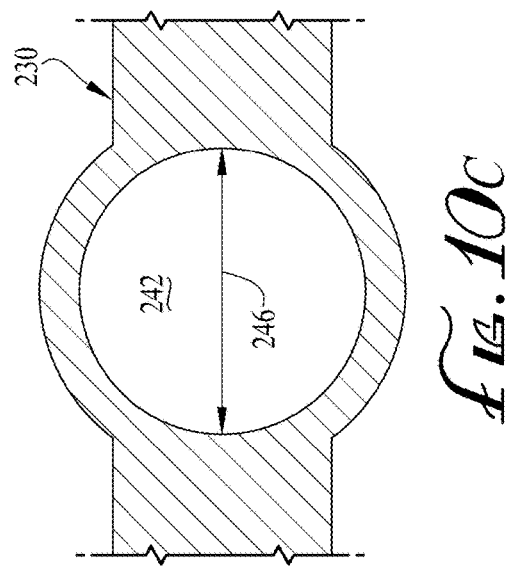
FIG. 10C shows the digital bar model segment of FIG. 10B.
Figure 10A:
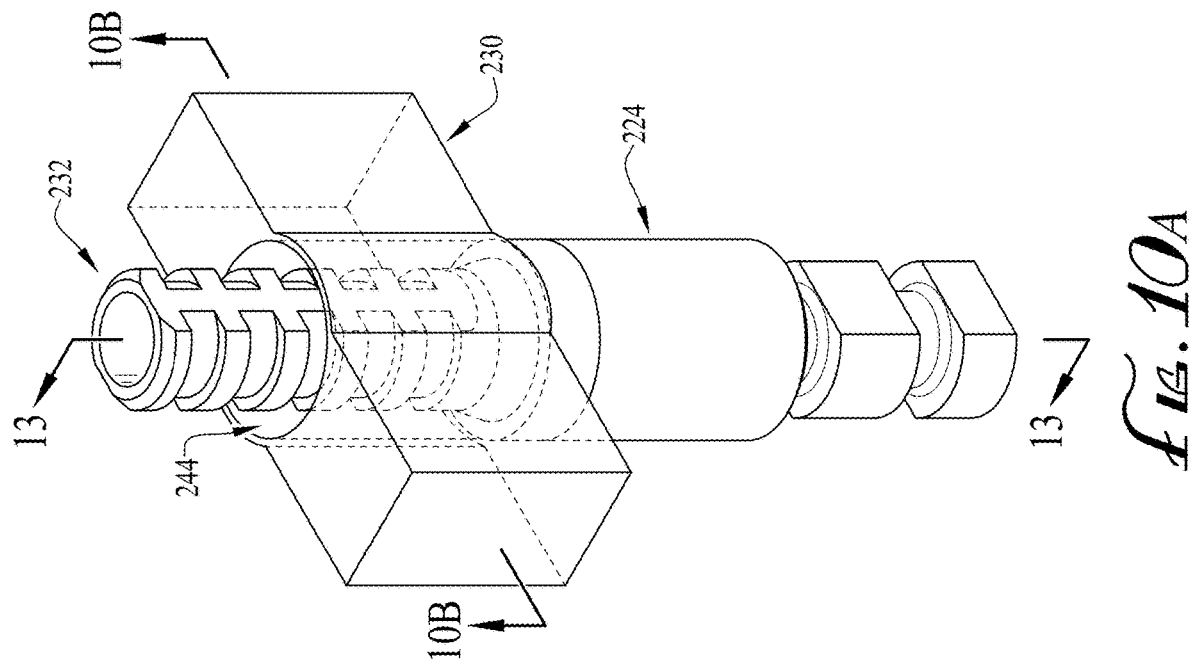
FIG. 10A is a screen display showing a segment of the digital bar model and one of the digital abutment models of FIG. 9.

FIGS. 10A-C in particular show a segment of the digital bar 230 having a vertical through-hole 242 that is oversized for a digital abutment 232 to provide a cement gap 244. That is, the vertical through-hole 242 has a minimum dimension (e.g., inner diameter) 246 that is sufficiently larger than a maximum dimension (e.g., outer diameter) 248 of a journal portion of the digital abutment 232 such that a cement gap 244 remains unoccupied to thereby permit discernable movement (i.e., colloquially, "play" or "wiggle room") of the bar on the abutment sufficient to provide a passive fit. As a reference for illustration purposes only, the bar vertical through-hole 242 can have an inner dimension 246 of about 0.155 inch to about 0.185 inch and the digital extension abutment 232 can have an outer diameter 248 of about 0.153 inch in order to provide a cement gap 244 gap of about 50 microns to about 802 microns total (about 25 microns to about 401 microns at each directly/diametrically opposite side, i.e., the radial or annular gap width). It will be understood that other cement gap annular widths can be used in this features, as well as that this digital cement gap design feature can be implemented in other denture bar methods (e.g., using other scanning equipment).

Figure 13:
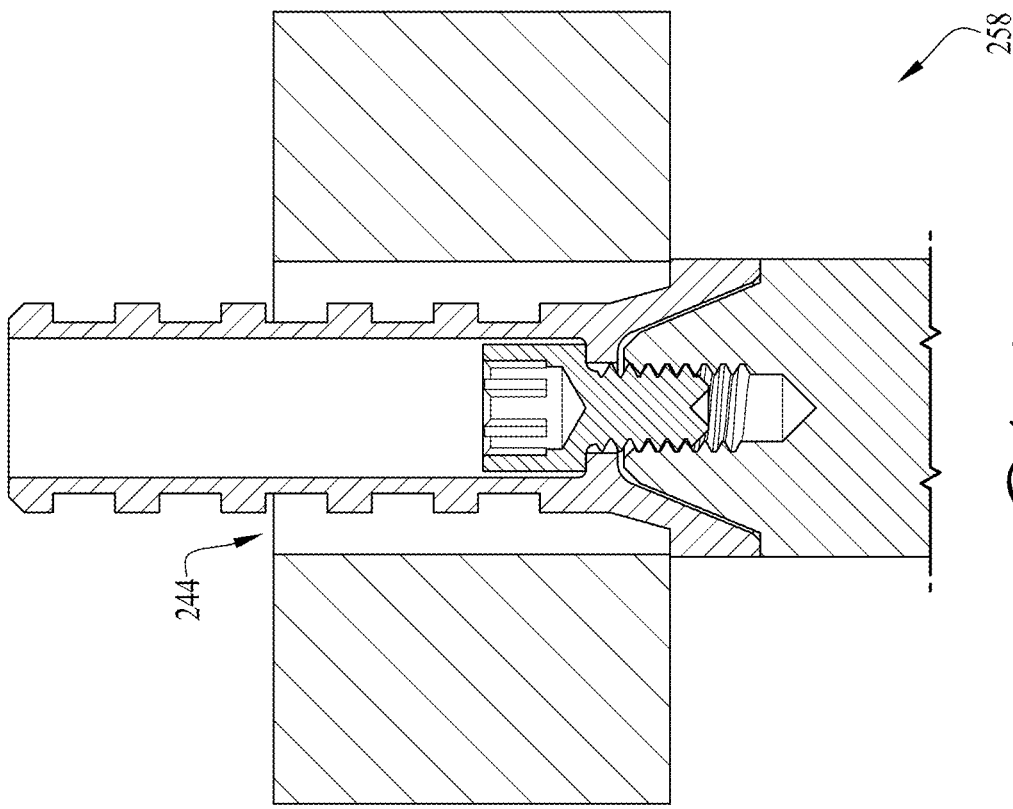
FIG. 13 is a screen display showing in cross-section the digital bar model segment and abutment of FIG. 10A with a loose spacing selected for the cement gap.
Figure 12:
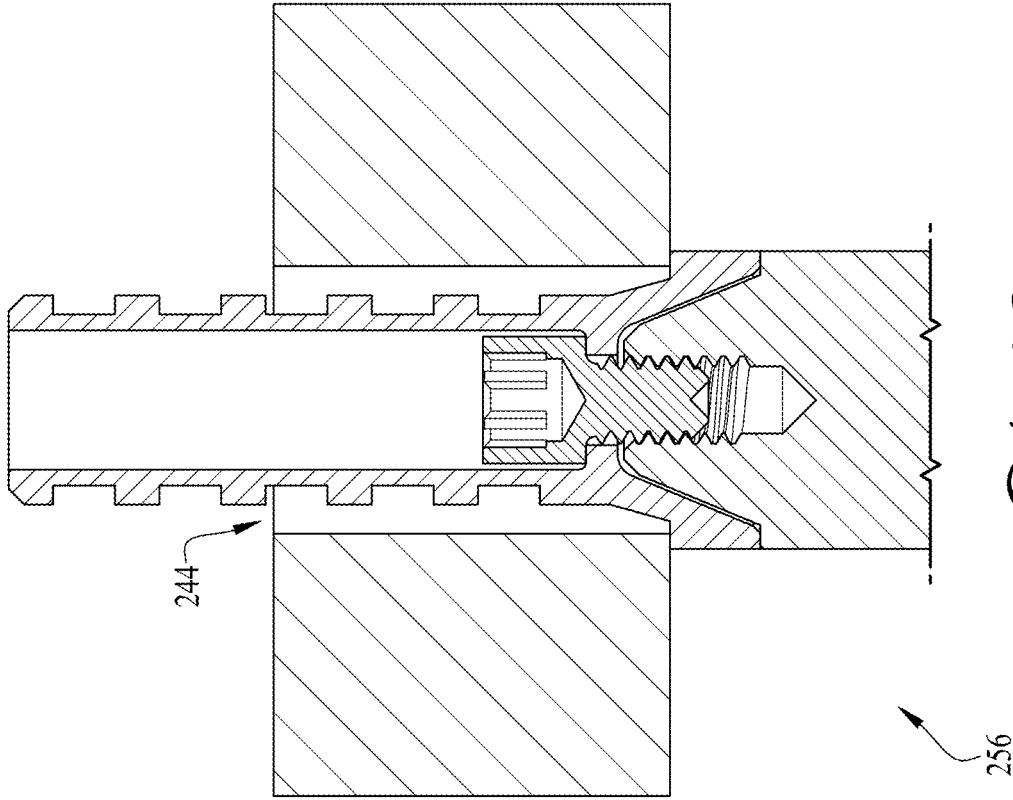
FIG. 12 is a screen display showing in cross-section the digital bar model segment and abutment of FIG. 10A with a standard spacing selected for the cement gap.

Returning to FIG. 9, the CAD software can be further set up with user-defined digital cement gaps 244 for use in designing the digital bars 230. For example, the depicted screenshot 250 shows a drop-down "spacing" menu 252 for a user to select from a "tight spacing," a "standard spacing," or a "loose spacing." In a corresponding manner, the screenshot 254 of FIG. 11 shows a cement gap 244 with a tight spacing (e.g., 25 microns total) selected, the screenshot 256 of FIG. 12 shows a cement gap 244 with a standard spacing (e.g., 100 microns total) selected, and the screenshot 258 of FIG. 13 shows a cement gap 244 with a loose spacing (e.g., 200 microns total) selected. In use, the technician can select a custom cement gap 244 for the digital bar 230 based on and to account for the magnitude of errors/inaccuracies in digital mouth model 220. A larger cement gap is selected when the scan of step 12 is done using an intraoral scanner, or even for a presurgical plan, than when the starting point was a scan of a non-verified model from a traditional polyvinyl impression (which provides greater precision and allows for a tighter fit providing easier delivery and requiring less cement).

The selected cement gap 244 can be predefined based on a percentage oversizing of the selected abutment 232, based on a predefined fixed-dimension oversizing of the selected abutment 232, or in another manner. Also, the selected cement gap 244 can be predefined with a uniform and symmetrical configuration, such as the annular cylinders depicted, or it can be configured in another regular or irregular shape, such as a frusto-conical annulus (i.e., tapered smaller in the gum-to-tooth direction).

Figure 14:
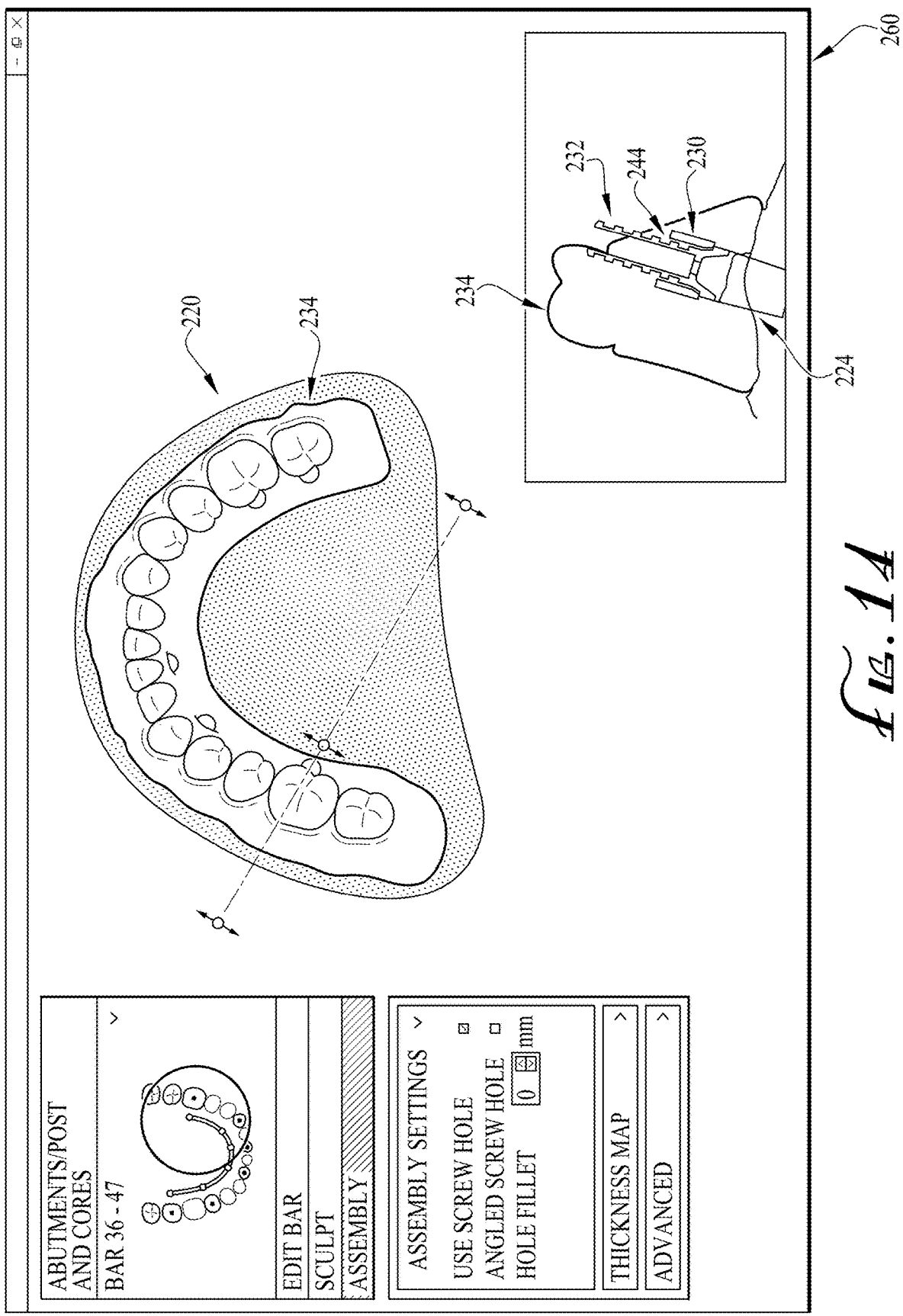
FIG. 14 is a screen display of the complete digital model of the mouth, bar, and denture of FIG. 8, with a cross-section inset showing a tight spacing of the cement gap between the abutment and the bar.
Figure 15:
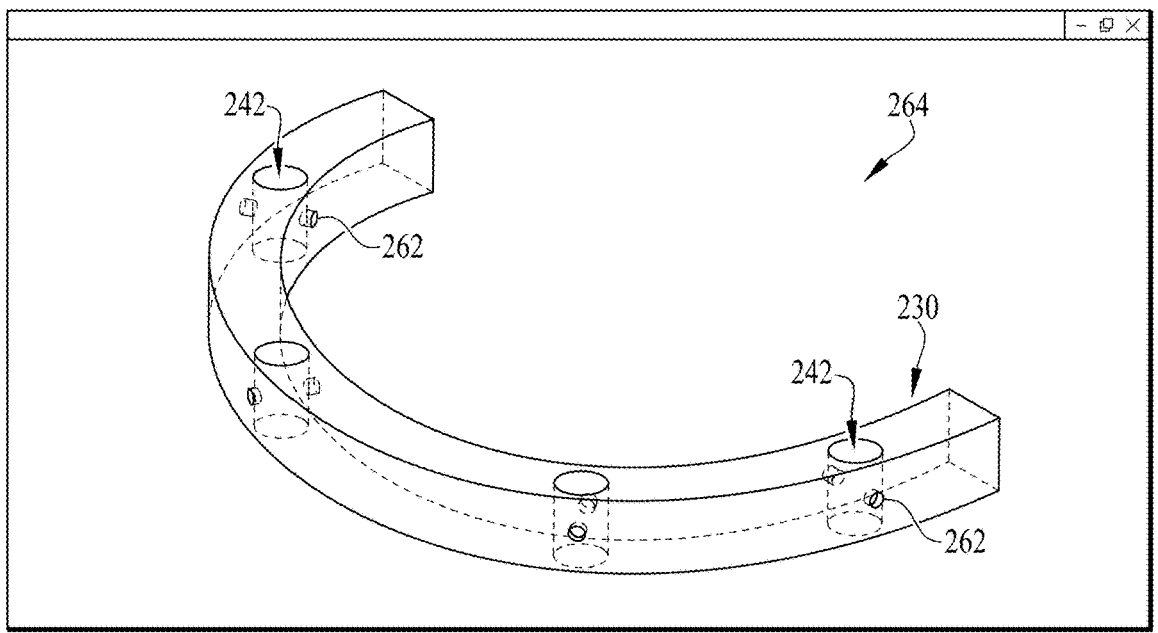
FIG. 15 is a screen display of an alternative-design digital bar model, showing lateral cement ports in the digital bar model formed transversely to the abutment holes in the bar.

The complete final digital assembly of the denture model 234 enclosing the digital bar 230, with the digital cement gaps 244 having a tight spacing for passive-fit mounting to the digital extension abutments 232, which are in turn mounted to the digital base abutments 224, is shown in the screenshot 240 of FIG. 14.

In another innovative aspect, the digital bar 230 can be digitally designed to include one or more lateral cement ports 262 extending transversely through the bar sidewall and in communication with the vertical through-holes in the bar. For example, in the screenshot 264 of FIG. 15, the bar 230 is designed with two aligned lateral cement ports 262 for each vertical through-hole 242 in the bar, with one port in the facial sidewall and the other axially aligned port in the opposite/lingual sidewall. (The depicted bar 230 is of an alternative design for illustration purposes but has the same essential elements as those previously depicted.) Additional details related the cement ports 262 are provided with respect to steps 18 and 20 below. In other embodiments, the lateral cement ports 262 are not included in the design of the bar but are formed as an additional step in the process of manufacturing the physical bar from the digital bar design using conventional manufacturing techniques (e.g., drilling). And in other embodiments, the lateral cement ports are not included in the design of the bar at all. It will be understood that this lateral cement port feature can be implemented in other denture bar methods.

Figure 16:
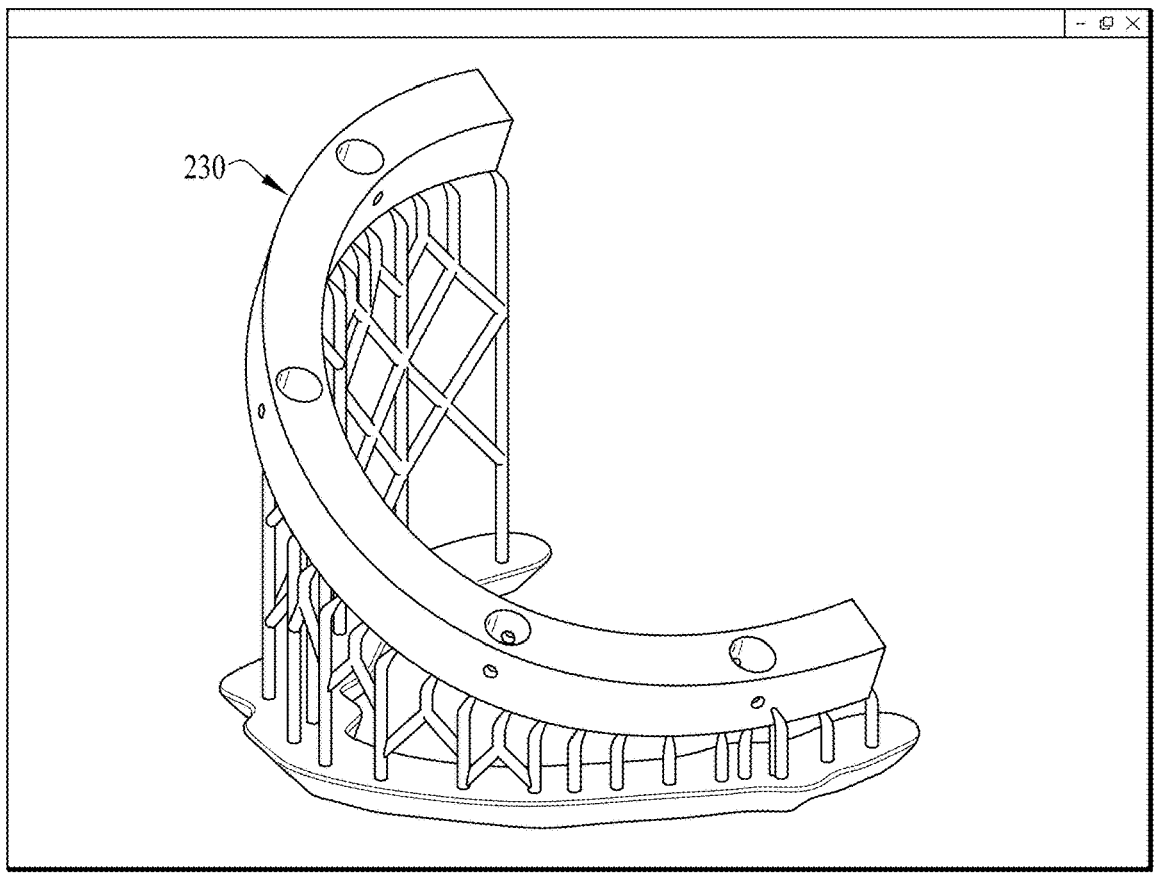
FIG. 16 is a screen display associated with an additive manufacturing process of a physical bar based on the digital bar model of FIG. 15, in accordance with a next step of the method.

Continuing with the method 10, at step 18 a physical bar is fabricated, using conventional CAM software, based on the digital bar design 230. The digital bar design 230 can be transmitted to a workstation and imported into the CAM software in any conventional well-known manner, with this step 18 typically being done at a remote production center. For example, the screenshot 266 of FIG. 16 shows the digital bar 230 being used to 3D print a physical bar in direct metal (e.g., an alloy of cobalt and chromium) using 3D-printing software inherently tied to the equipment. Additive manufacturing processes such as 3D printing are advantageous for fabrication of the physical bar because they permit easily forming both the vertical through-holes and the lateral cement ports in the same continuous process (without needing a two-step process). It will be understood that the physical bar can be manufactured from the digital bar using other conventional techniques, such as milling, machining, and other subtractive manufacturing processes, as well as hybrid processes combining multiple of these processes.

Figure 17:
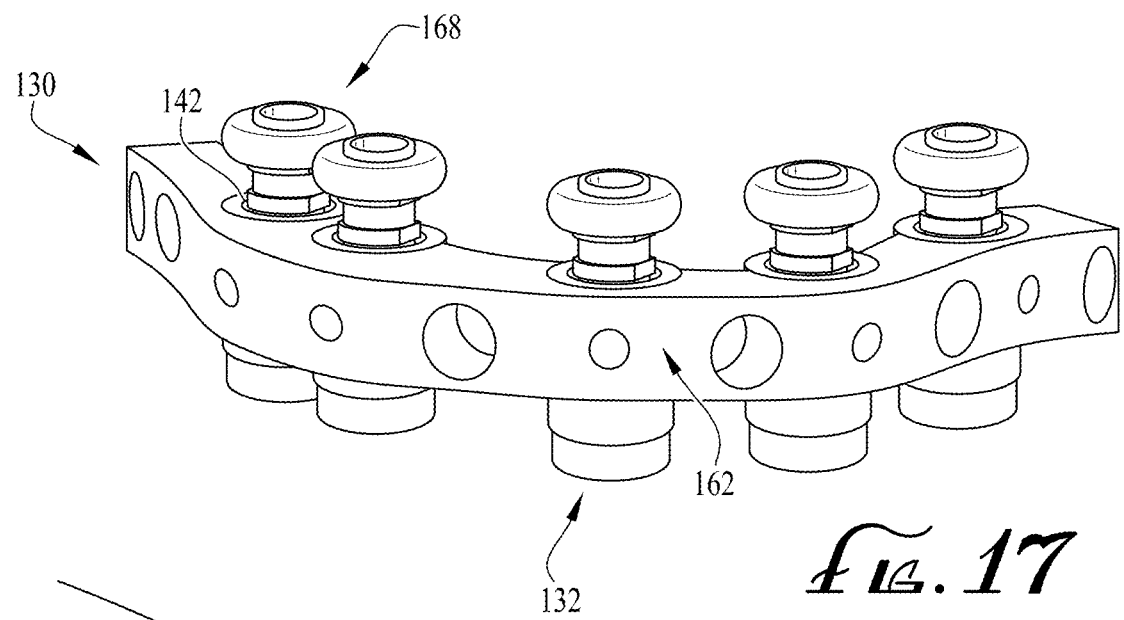
FIG. 17 is a perspective view of an alternative-design physical bar, with physical extension abutments positioned in the abutment holes and ready for installation in a second office visit.

FIG. 17 shows the resulting fabricated physical bar 130, with the selected physical extension abutments 132 assembled onto it and secured there ready for intraoral delivery. (The depicted bar 130 is of an alternative design for illustration purposes but has the same essential elements as those previously depicted.) The abutments 132 each have a journal/upper portion that extends through a respective vertical through-hole 142 and an exposed upper end with a retainer 168 with a larger maximum lateral dimension (e.g., diameter) than the through-hole so that the abutment cannot slide down through the oversized through-hole and separate from the bar 130. As depicted, each retainer 168 is a resilient (e.g., rubber or plastic) O-ring that seats into a circumferential groove in the respective abutment 132 and that can be easily installed (e.g., rolled or pushed on under stretching/deforming forces by a user's finger) onto the abutment. In other embodiments, the retainers are deflectable (e.g., PEEK or another plastic) snap-rings (e.g., C-shaped) for a similar seated fit, mating threads on the bar and abutments, or of a press-fit assembly. In this way, the retainers 168 can be provided as separate pieces and installed onto the abutments 132 after they have been inserted into their respective through-holes 142. And in other embodiments, the bar and the abutments are provided to the dentist as a loose assembly of parts, not held together by any means. It will be understood that this retainer feature can be implemented in other denture bar methods.

Figure 18:
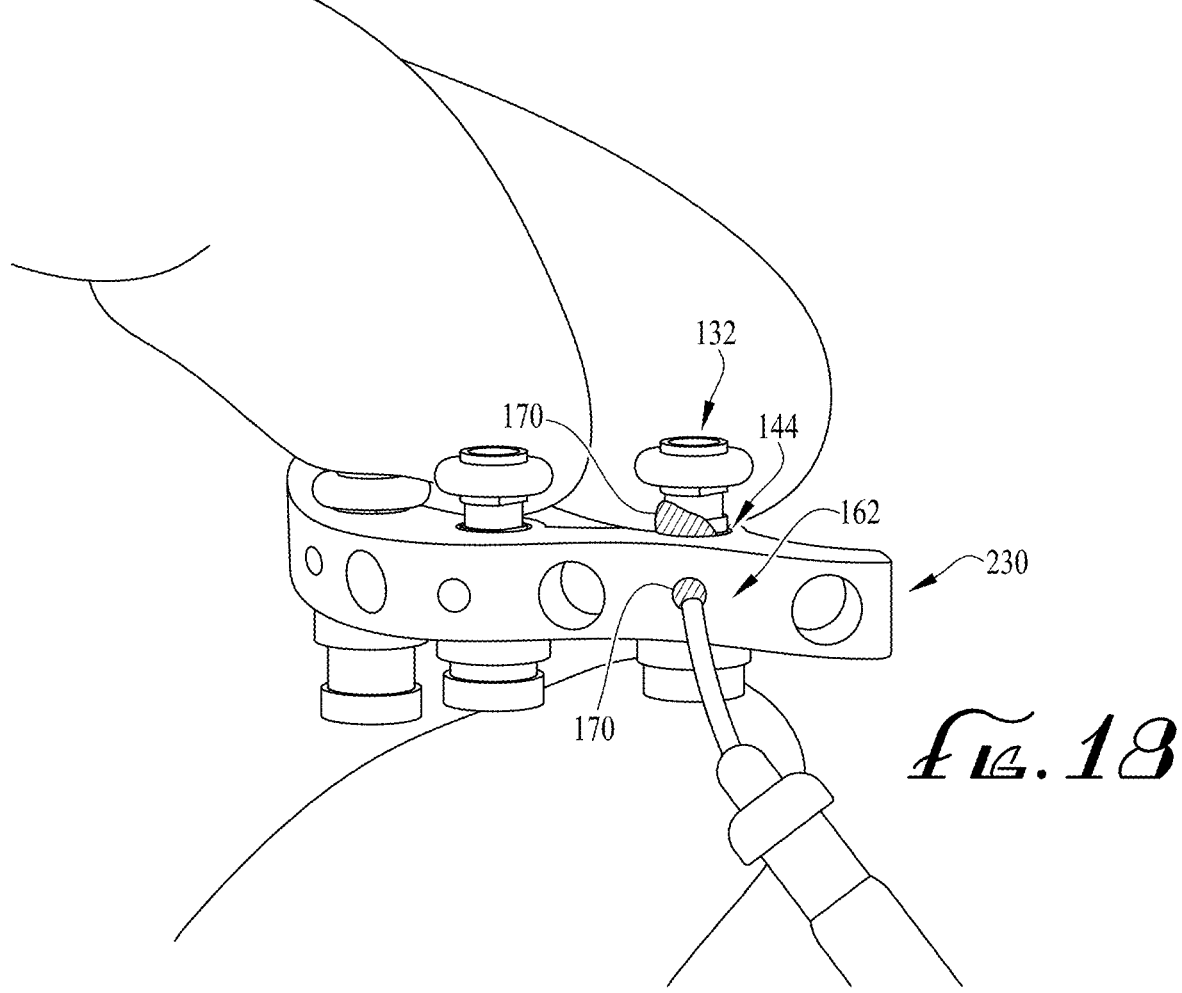
FIG. 18 is a perspective view of the physical bar and abutments of FIG. 17, showing cement being injected into the cement gaps via the cement ports in an extra-oral process, in accordance with a next step of the method.

Next at step 20, the combined bar-and-abutment assembly (the physical bar 130 with the selected physical extension abutments 132 assembled onto it and secured there by the retainers 162) is ready for intraoral delivery into the patient's mouth 120 in a second dentist's office visit. In the traditional luting process, the cement is applied intraorally directly to the physical abutments in the patient's mouth and then the physical bar is mounted onto them. Instead, as shown in FIG. 18, the clinician can extraorally apply the cement 170 by injecting it (e.g., via a syringe) through the cement ports 162 and into the cement gaps 144 in the bar 130 while the abutments 132 are assembled in place in the bar through-holes 142. The bar-and-abutment assembly can be grasped by the bottoms of the abutments 132 and the top of the bar 130 so that the abutments 132 are at their raised-most positions with the wider base portions of the abutments 132 abutting and blocking the bottom of the annular cement gaps 142, as shown. In this way, when the cement gaps 144 are filled with the cement 170, all excess cement 170 is expelled through the tops of the annular cement gaps 142, with none able to exit through the blocked bottoms. This keeps excess cement 170 away from the patient's gum-line 121 upon intraoral delivery of the bar-and-abutment assembly 130/132 and this makes cleaning away the excess cement easier.

Then the bar-and-abutment assembly 130/132 is inserted into the patient's mouth 120 by the clinician, with the retainers 168 ensuring that the abutments 132 do not slide down and fall out of the through-holes 142 (and to the floor or into the patient's mouth). The bottoms of the retained extension abutments 132 are then placed onto the tops of the base abutments 124, and the cement 170 is then cured (e.g., by time and/or UV light) intraorally in situ, to fix the position of the bar 130 relative to the abutments 132. In other embodiments, the bar-and-abutment assembly is delivered into the mouth and fixed in place, and then the cement is intraorally applied to the assembly where it cures, regardless of whether or not the bar includes lateral cement ports.

Figure 19:
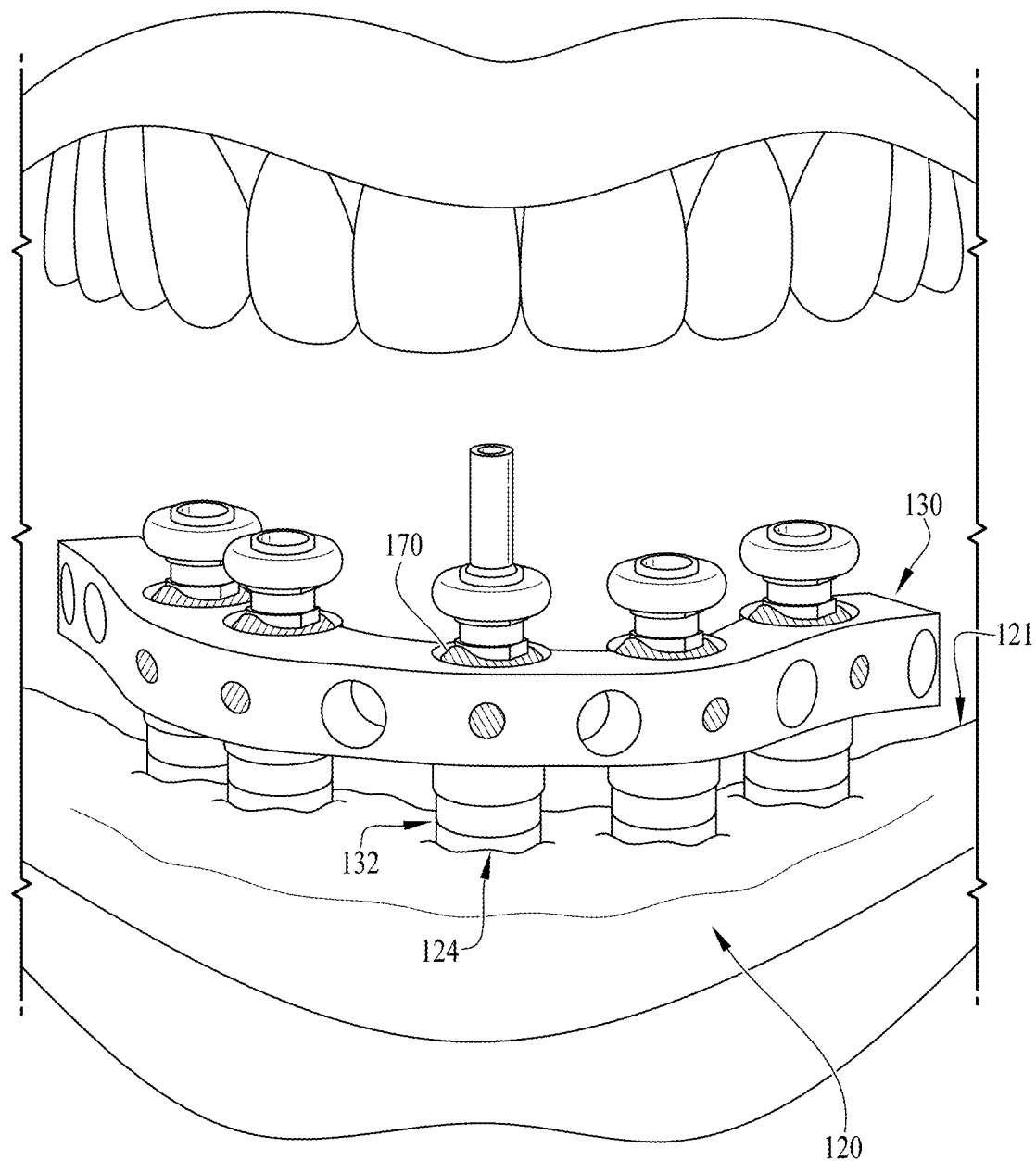
FIG. 19 is a perspective view of the physical bar and abutments of FIG. 18 after cement curing and installation onto the base abutments, with the bar being checked to confirm a passive fit.
Figure 20:
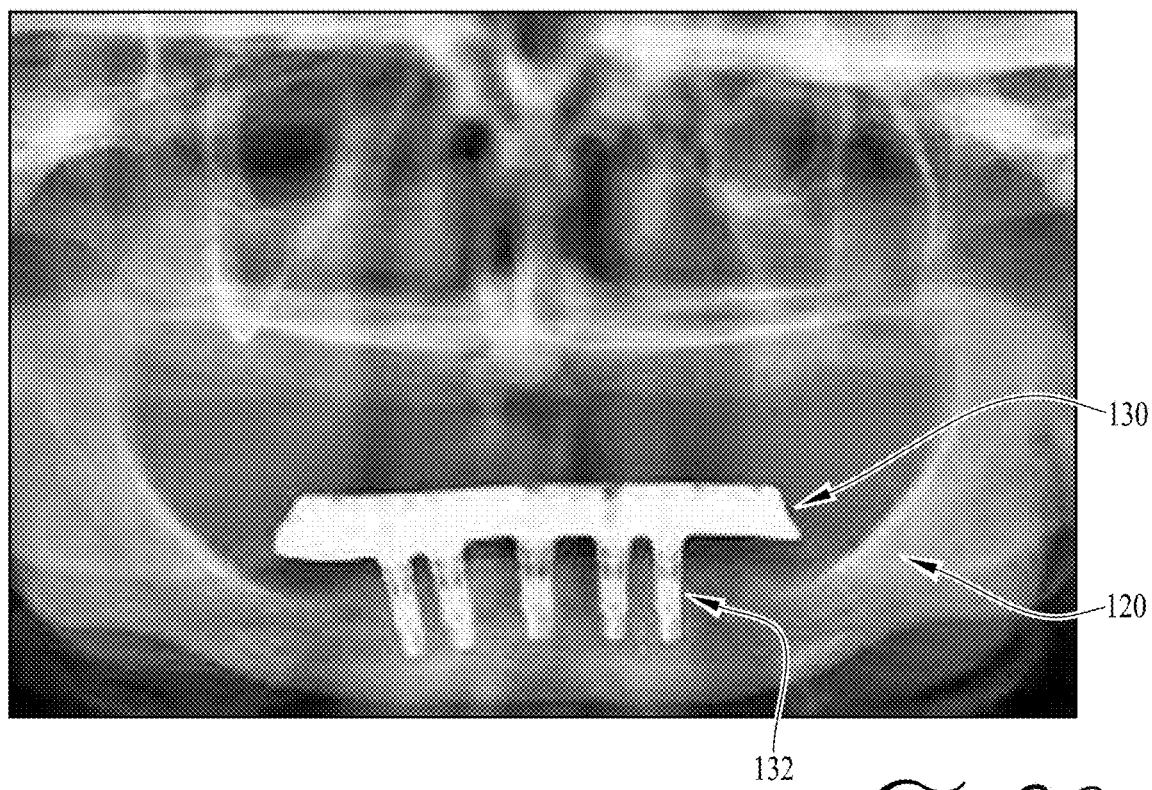
FIG. 20 is a radiographic image of the final installation of the physical bar and abutments of FIG. 19 in the patient's mouth, after the excess lengths of the abutments above the bar have been trimmed off.

The cured bar-and-abutment assembly 130/132 is traditionally verified for a passive fit by fixedly attaching (e.g., by a mounting screw) one of the extension abutments 132 in place and confirming that the bar 130 remains in place and is not displaced vertically as the connection is tightened (i.e., using the Sheffield test), as shown in FIG. 19. The other extension abutments 132 are then fixedly attached to their respective base abutments 124, the assembly is removed and the excess lengths of the abutments 132 are trimmed (i.e., the journal portion extending above the top of the bar 130 is removed), and the assembly is reinstalled in the mouth. Verification can be obtained by taking a radiographic image of the bar-and-abutment assembly 130/132, as shown in FIG. 20. The bar-and-abutment assembly 130/132 is now complete (constructed into an integral appliance) and ready for use.

Figure 21:
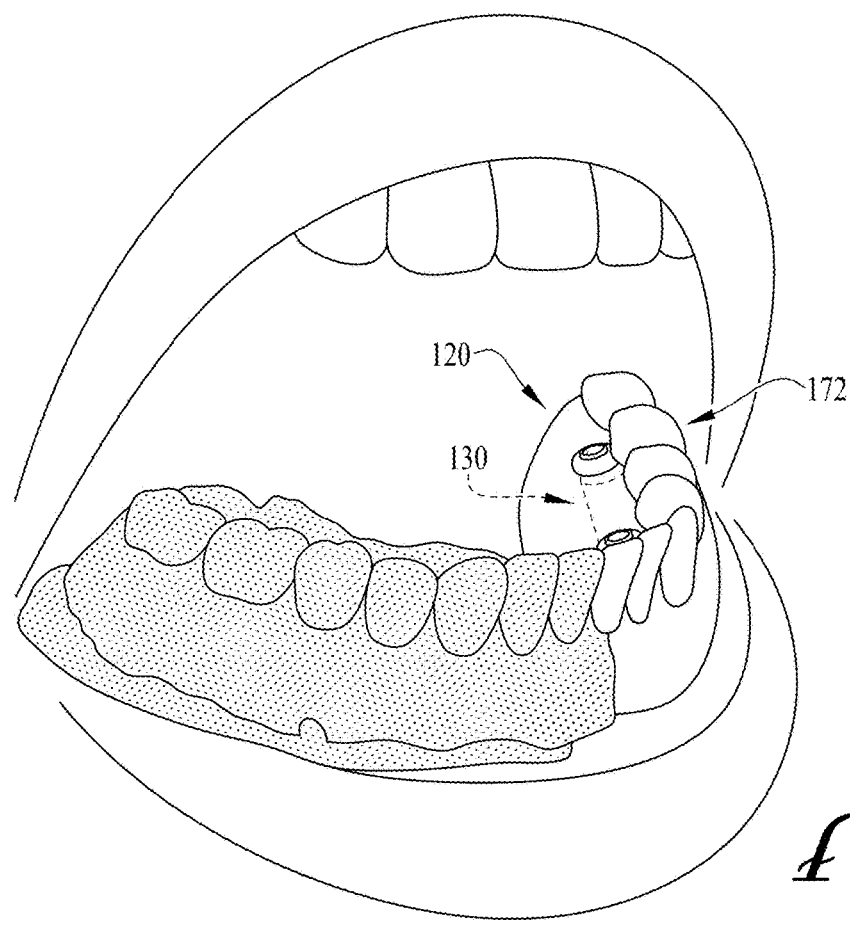
FIG. 21 is a perspective view of an alternative-design physical bar, with a model of a physical denture shown partially filled with molding material, in accordance with a next step of the method.
Figure 22:
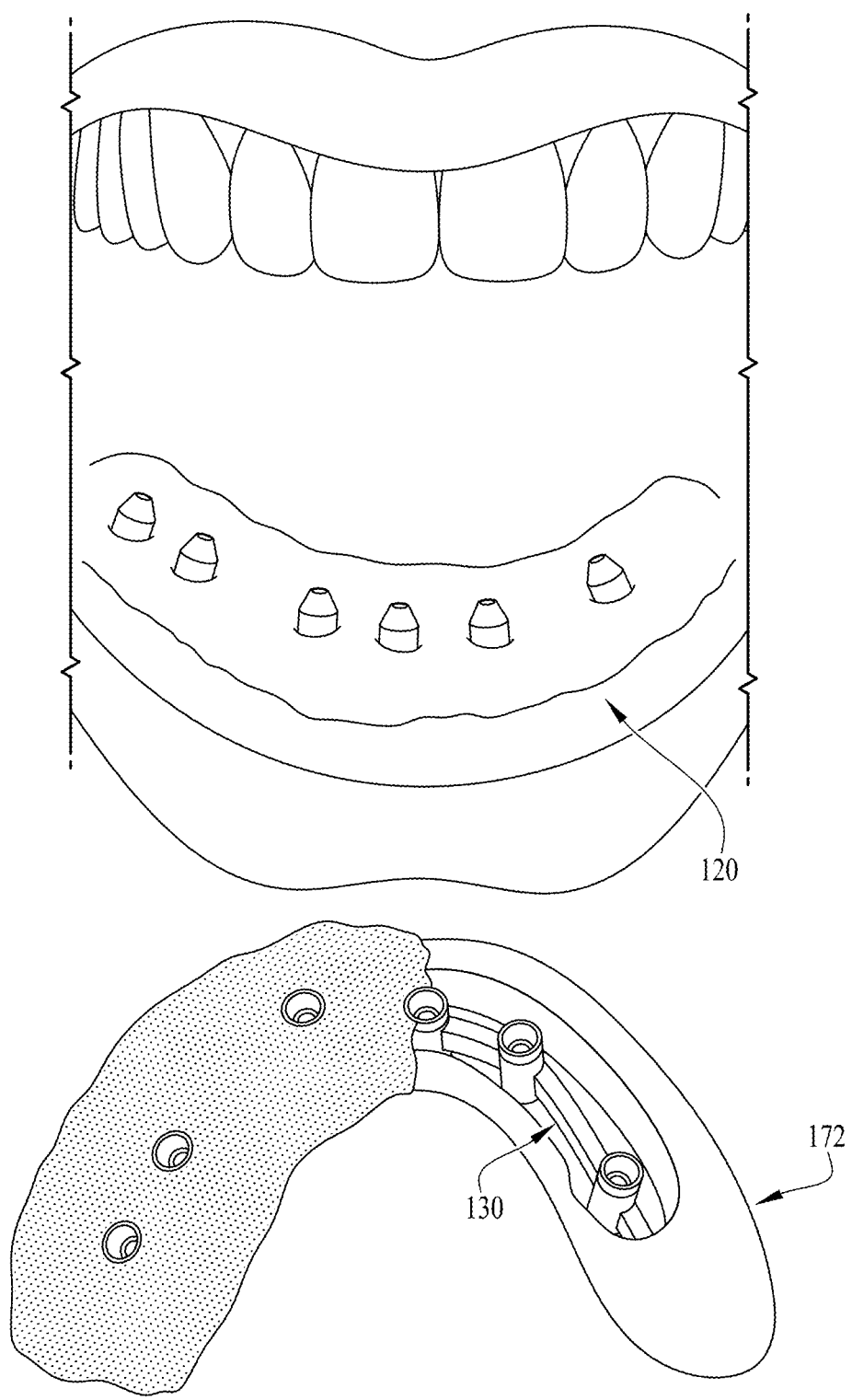
FIG. 22 is a perspective view of the physical bar and partially filled denture model of FIG. 21 disassembled to show the underside of the denture and the bar.

At step 22, records are captured of the bar-and-abutment assembly 130/132 in the patient's mouth 120 for use in fabricating the denture 134. The record capture step 22 can be accomplished by a conventional process known in the art. For example, the record capture 22 can be done using an impression tray 172 made of a shell having an outer contour conforming to the shape of the denture 134 and an inner space for receiving the bar 130 and conventional mold material, as shown in FIGS. 21-22. (The depicted bar 130 is of an alternative design for illustration purposes but has the same essential elements as those previously depicted.) This step 22 can be done during the same/second office visit.

Figure 23:
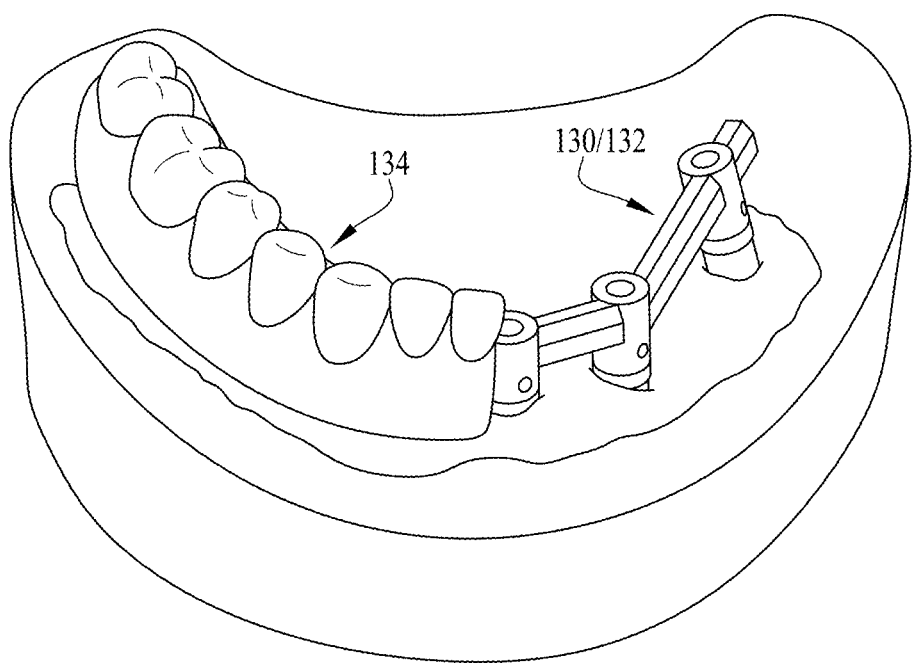
FIG. 23 is a perspective view of a denture formed based on the physical bar and denture model of FIG. 22, with a portion cutaway to revel the internal bar, in accordance with a next step of the method.

Next at step 24, the captured records are used to fabricate the physical denture 134 joined to and surrounding the bar 130 (the top and sides only, leaving the bottoms of the extension abutments 132 exposed for connecting to the base abutments 124). This step 24 can be accomplished by a conventional process known in the art. For example, FIG. 23 shows a denture 134 that has been formed based on the bar 130 and the denture model 174, with a portion of the denture removed to show the internal bar, with the resulting denture-and-bar assembly 134/130 now being constructed into an integral appliance. This step 24 is typically done after the second patient visit, by a dental technician at a remote lab, though it can be done at the local dentist's office.

Figure 25:
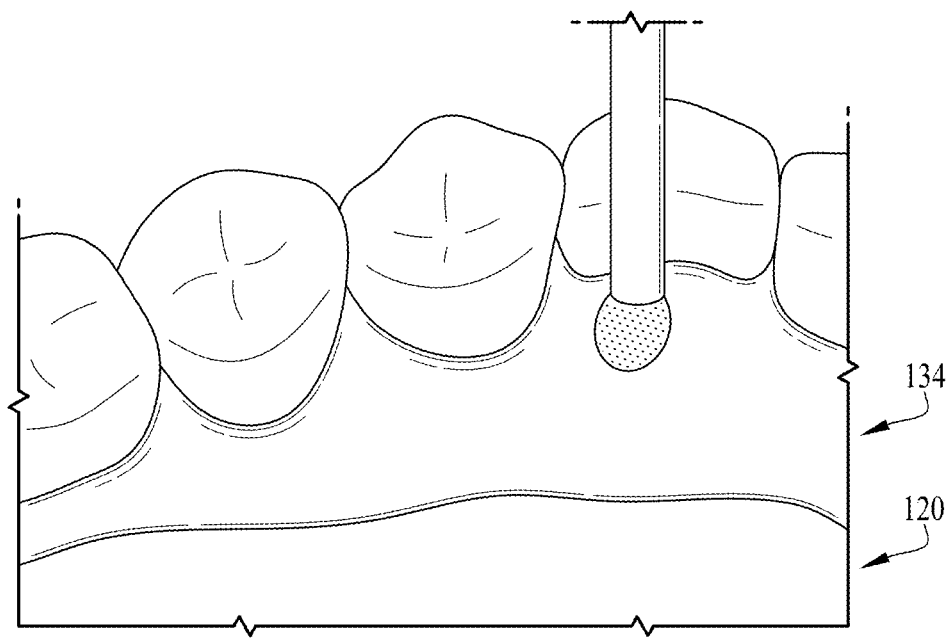
FIG. 25 is a perspective detail view of the physical bar and denture installation of FIG. 24.
Figure 24:
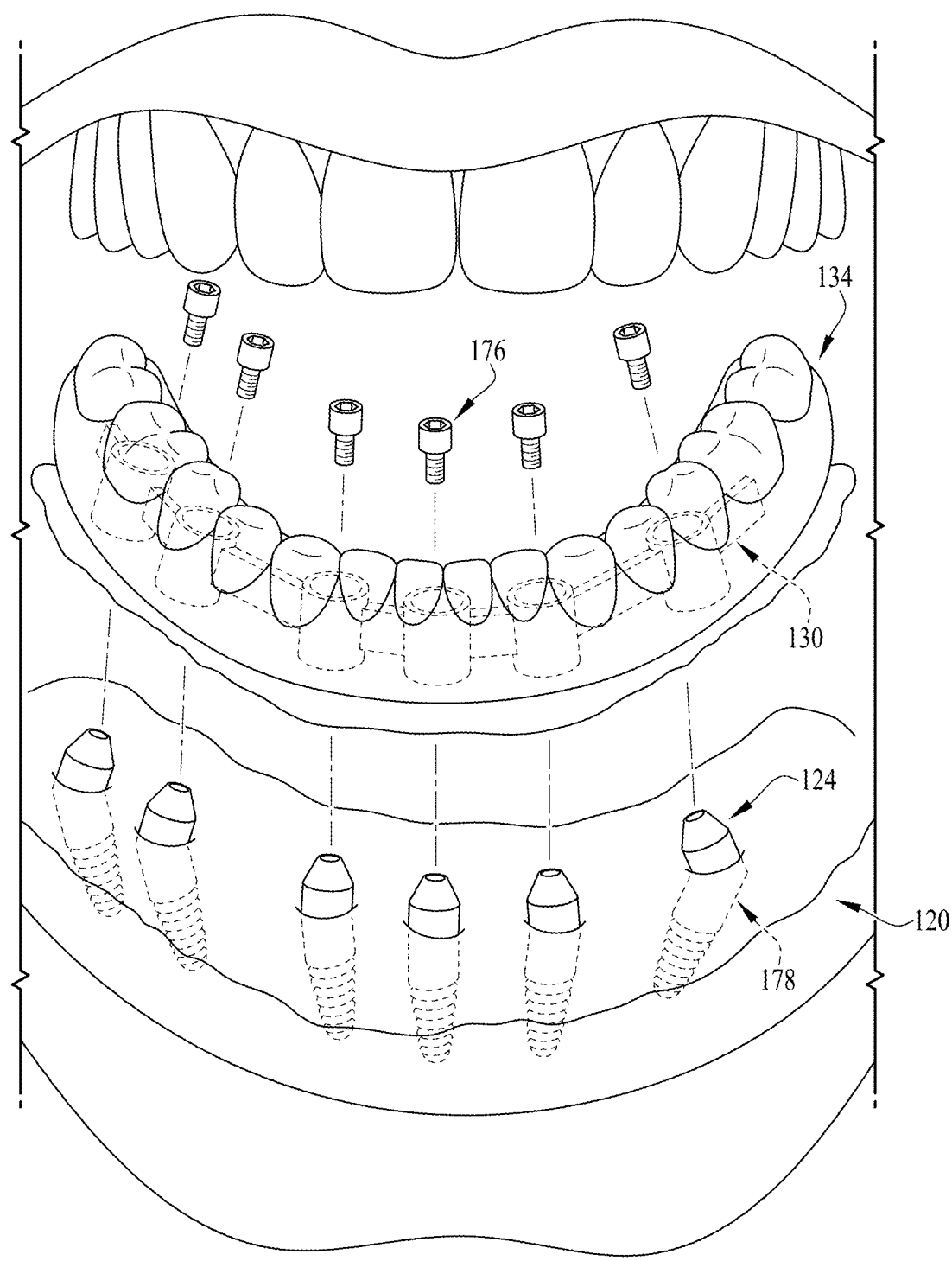
FIG. 24 is a perspective view of an alternative-design physical bar and denture being installed in the patient's mouth in a third office visit, in accordance with a next step of the method.

Finally at step 26, the finished denture-and-bar assembly 134/130 is delivered intraorally into the patient's mouth 120 for permanent installation in a third dentist's office visit. This step 26 can be accomplished by a conventional process known in the art. For example, FIGS. 24-25 show mounting screws 176 that fixedly attach the bar 130 (and thus the denture 134 fixedly formed onto it, via the extension abutments 132) to the base abutments 124 (which in turn are mounted to the implants 178 secured in the patient's jawbone). (The depicted bar 130 and abutments 124 are of an alternative design for illustration purposes but have the same essential elements as those previously depicted.) As such, the entire implant denture bar process 10 can be completed in only three patient visits to the dentist's office.

If guided surgery is used, the software "assumes" the position of the implants to create a pre-surgical digital model of the patient identical to that shown in FIG. 4. This can preclude the need for an intraoral scan, and allow the doctor to, in the first appointment, not only deliver the implants by way of a surgical guide, but also the bar immediately afterwards. Thus, in this embodiment of the method, the first appointment includes placement of the prerequisite implants (and abutments if applicable) as well as delivery of the bar, with the process then completed in only two visits. In another aspect, the invention relates to a physical denture bar designed and made according to the method 10. As noted above, for example, the physical bar 130 can be provided with the selected physical extension abutments 132 assembled onto it and secured there by retainers 168 ready for intraoral delivery (see FIG. 17). In other embodiments, the bar is provided by itself with the abutments provided separately, the abutments are provided without the retainer, and/or the bar and the abutments are provided together but loose (unassembled). In any of these embodiments, the bars can be provided with or without the lateral cement ports 162.

In other aspects, the invention relates to methods for digitally designing a denture bar (e.g., by a dentist or dental technician), according to the methods described herein, with the digital bar design used for manufacturing and installing a physical bar according to herein-described or other methods; methods for manufacturing a physical denture bar (e.g., at a remote production center), according to the methods described herein, with the physical bar designed and installed according to herein-described or other methods; and methods for installing a physical denture bar (e.g., by a dentist or dental technician), according to the methods described herein, that was digitally designed and manufactured according to herein-described or other methods.

While the invention has been described with reference to example embodiments, it will be understood by those skilled in the art that a variety of modifications, additions and deletions are within the scope of the invention, as defined by the following claims.

What is claimed is:

1. A denture bar method, comprising:
taking an intraoral scan directly of a patient's mouth with existing abutments;
creating a digital mouth model of the patient's mouth based on the intraoral scan, the digital mouth model including digital abutments based on the existing abutments;
digitally designing a denture bar based on the digital mouth model, including digitally designing a plurality of vertical through-holes in the digital denture bar for receiving the digital abutments therethrough, digitally designing an oversized cement gap for each of the vertical through-holes, and digitally designing lateral cement ports through a sidewall of the digital denture bar and in communication with the vertical through-holes, wherein the oversized cement gaps surround the vertical through-holes and enable the vertical through-holes to provide a fit for the respective digital abutments with space for receiving cement and with additional space to allow for errors in the digital mouth model resulting from the intraoral scan;

fabricating a physical denture bar based on the digital denture bar, including fabricating vertical through-holes with oversized cement gaps in the physical denture bar that correspond to the digital vertical through-holes and oversized cement gaps, and fabricating lateral cement ports in the physical denture bar that correspond to the digital lateral cement ports and are in communication with the vertical through-holes;

delivering the physical denture bar into the patient's mouth;

capturing records of the patient's mouth and installed physical denture bar, then removing the physical denture bar from the patient's mouth;

producing a physical denture for the physical denture bar; and delivering the physical denture and the physical denture bar into the patient's mouth, including placing the existing abutments into the respective vertical through-holes of the physical denture bar, and injecting the cement through the lateral cement ports in the physical denture bar and into the cement gaps in the physical denture bar while the existing abutments are positioned in the respective vertical through-holes of the physical denture bar.

2. The denture bar method of claim 1, wherein:

the step of taking an intraoral scan directly of a patient's mouth with the existing abutments is performed during a first dental office visit;

the step of delivering the physical denture bar into the patient's mouths is performed during a second dental office visit; and the step of delivering the physical denture and denture bar into the patient's mouth is performed during a third dental office visit, wherein the denture bar method includes no more dental office visits than the three dental office visits.

3. The denture bar method of claim 1, wherein the step of digitally designing a denture bar is performed using CAD software and the step of fabricating a physical bar is performed using CAM software.

4. The denture bar method of claim 1, wherein the step of digitally designing an oversized cement gap further includes selecting an oversized cement gap from a library of cement gap spacings to provide a custom oversizing for the passive fit.

5. The denture bar method of claim 1, wherein the step of digitally designing an oversized cement gap further includes selecting an oversized cement gap of about 25 microns to about 400 microns in annular width.

6. The denture bar method of claim 1, wherein the step of injecting cement through the lateral cement ports includes holding the existing abutments in raised-most positions in the vertical through-holes during the injecting so that excess cement is expelled through tops of the cement gaps.

7. The denture bar method of claim 1, wherein the step of delivering the physical denture bar includes inserting the existing abutments through the vertical through-holes and then attaching retainers to upper portions of the existing abutments extending above the physical denture bar to enable the existing abutments to slide within the respective through-holes but to prevent the existing abutments from falling downward out of the vertical through-holes.

8. A denture bar method comprising:

taking an intraoral scan directly of a patient's mouth with existing abutments during a first dental office visit;

creating a digital mouth model of the patient's mouth based on the intraoral scan, the digital mouth model including digital abutments based on the existing abutments;

digitally designing a denture bar based on the digital mouth model and using CAD software, including digitally designing a plurality of vertical through-holes in the digital dental bar sized for receiving respective digital abutments therethrough, and including digitally designing an oversized cement gap for each of the vertical through-holes so that the vertical through-holes are oversized to provide a fit for the respective digital abutments with space to allow for errors in the digital mouth model resulting from the intraoral scan in addition to space for insertion of cement;

obtaining the physical denture bar fabricated based on the digital denture bar and using CAM software;

delivering the physical denture bar into the patient's mouth during a second dental office visit;

capturing records of the patient's mouth and installed physical denture bar, then removing the physical denture bar from the patient's mouth;

producing a physical denture and joining it to the physical denture bar; and delivering the physical denture and denture bar into the patient's mouth during a third dental office visit, wherein the denture bar method includes no more dental office visits than the three dental office visits, wherein the step of digitally designing a cement gap further includes selecting the cement gap from a library of cement gap spacings to provide a custom oversizing, wherein the step of digitally designing the denture bar further includes digitally designing lateral cement ports through a sidewall of the digital bar and in communication with the vertical through-holes, and wherein the step of delivering the physical denture bar includes injecting the cement through lateral cement ports in the physical denture bar that correspond to the digital lateral cement ports, and into cement gaps in the physical denture bar that correspond to the digital cement gaps, while the respective existing abutments are positioned in the respective vertical through-holes.

9. The denture bar method of claim 8, wherein the step of injecting cement through the lateral cement ports includes holding the existing abutments in raised-most positions in the vertical through-holes during the injecting so that excess cement is expelled through tops of the cement gaps.

10. The denture bar method of claim 8, wherein: the step of delivering the physical bar includes inserting the existing abutments though the vertical through-holes and then attaching retainers to upper portions of the existing abutments extending above the physical denture bar to enable the existing abutments to slide within the respective through-holes but to prevent the existing abutments from falling downward out of the vertical through-holes; wherein the step of injecting cement through the lateral cement ports includes holding the existing abutments in raised-most positions in the vertical through-holes during the injecting so that excess cement is expelled through tops of the cement gaps.

11. A denture bar method, comprising:

creating a physical model of a patient's mouth with existing abutments and taking an indirect scan of the physical mouth model;

creating a digital mouth model of the patient's mouth based on the indirect scan, the digital mouth model including digital abutments based on the existing abutments;

digitally designing a denture bar based on the digital mouth model, including digitally designing a plurality of vertical through-holes in the digital denture bar for receiving the digital abutments therethrough, digitally designing an oversized cement gap for each of the vertical through-holes, and digitally designing lateral cement ports through a sidewall of the digital denture bar and in communication with the vertical through-holes, wherein the oversized cement gaps surround the vertical through-holes and enable the vertical through-holes to provide a fit for the respective digital abutments with space for receiving cement and with additional space to allow for errors in the digital mouth model resulting from the intraoral scan;

fabricating a physical denture bar based on the digital denture bar, including fabricating vertical through-holes with oversized cement gaps in the physical denture bar that correspond to the digital vertical through-holes and oversized cement gaps, and fabricating lateral cement ports in the physical denture bar that correspond to the digital lateral cement ports and are in communication with the vertical through-holes;

delivering the physical bar into the patient's mouth;

capturing records of the patient's mouth and installed physical bar, then removing the physical denture bar from the patient's mouth;

producing a physical denture for the physical denture bar; and delivering the physical denture and the physical denture bar into the patient's mouth, including inserting the existing abutments into the respective vertical through-holes of the physical denture bar, and injecting the cement through the lateral cement ports in the physical denture bar and into the cement gaps in the physical denture bar while the existing abutments are positioned in the respective vertical through-holes.

\* \* \* \* \*